United States Patent [19]
Ankersen et al.

[11] Patent Number: 6,127,343
[45] Date of Patent: Oct. 3, 2000

[54] SOMATOSTATIN AGONISTS AND ANTAGONISTS

[75] Inventors: Michael Ankersen, Frederiksberg; Carsten Enggaard Sitdsen, Bagsvaerd; Henrik Sune Andersen, Copenhagen, all of Denmark

[73] Assignee: Novo Nordisk A/S, Bagsværd, Denmark

[21] Appl. No.: 08/855,781

[22] Filed: May 12, 1997

Related U.S. Application Data

[60] Provisional application No. 60/031,867, Jul. 17, 1996.

[30] Foreign Application Priority Data

May 14, 1996 [DK] Denmark ................... 0576/96

[51] Int. Cl.⁷ ............... A61K 38/00; C07K 5/00; C07K 7/00
[52] U.S. Cl. ............................. 514/20; 530/311
[58] Field of Search ................... 514/20; 530/311

[56] References Cited

U.S. PATENT DOCUMENTS 5,021,431  6/1991  Buschauer et al. .

FOREIGN PATENT DOCUMENTS

| | | |
|---|---|---|
| 0 488 765 | 10/1991 | European Pat. Off. . |
| 36 31 334 | 3/1988 | Germany . |
| WO 87/07891 | 12/1987 | WIPO . |
| 9743278 | 11/1997 | WIPO .................... C07D 401/12 |

*Primary Examiner*—Avis M. Davenport
*Attorney, Agent, or Firm*—Steve T. Zelson, Esq.; Elias J. Lambiris, Esq.; Carol Rozek, Esq.

[57] ABSTRACT

The present invention relates to compounds, compositions containing them, and their use for treating medical disorders related to binding to human somatostatin receptor subtypes.

17 Claims, No Drawings

SOMATOSTATIN AGONISTS AND ANTAGONISTS

CROSS-REFERENCE TO RELATED APPLICATIONS

This application claims priority under 35 U.S.C. 119 of Danish application serial no. 0576/96 filed May 14, 1996 and U.S. application Ser. No. 60/031,867 filed Jul. 17, 1996, the contents of which are fully incorporated herein by reference.

FIELD OF INVENTION

The present invention relates to compounds, compositions containing them, and their use for treating medical disorders related to binding to human somatostatin receptor subtypes.

BACKGROUND OF THE INVENTION

Somatostatin (somatotropin release inhibiting factor; SRIF), a tetradecapeptide originally isolated from ovine hypothalamus on the basis of its ability to inhibit growth hormone release from anterior pituitary cells (Brazeau, P. et al., Science 179, 77–79, 1973) has been shown to be present in several other tissues (for a review see Reichlin, S., N. Engl. J. Med. 309, 1495–1501, 1983 and ibid, 1556–1563). Somatostatin appears to have widespread functions as a modulator of neuronal activity as well as of endocrine and exocrine secretion. Inhibitory effects of this peptide on the release of a variety of hormones such as growth hormone, prolactin, glucagon, insulin, gastrin and thyroid stimulating hormones have been described (for a review see Wass, J. A. H., in Endocrinology, ed. deGrott, L. J., vol 1, 152–166, 1989). Somatostatin is best regarded as belonging to a phylogenetically ancient, multigene family of peptides with two important bioactive products, namely SRIF-14 (SRIF) and SRIF-28, a congener of SRIF extended at the N-terminus.

The regulatory functions of SRIF are mediated by specific membrane receptors. Currently, only agonists are available to study the pharmacology of SRIF receptors. High-affinity saturable binding sites have been demonstrated in a number of tissues, e.g. pituitary gland, brain and pancreas. Within the last few years the cloning and isolation of five somatostatin receptor genes has been reported for various species (human, rat, mouse and bovine). Structural analysis of the encoded proteins revealed that the somatostatin receptor proteins (SST1–SST5) represent a distinct receptor subfamily (named the A5 subfamily) belonging to the superfamily of G protein-coupled receptors with seven putative membrane spanning regions.

Recent work on the development of nonpeptide structures substituting the peptide backbone of small cyclic peptides with a β-D-glucose scaffold (Hirschmann, R. et al., J.Am. Chem.Soc. 115, 12550–12568, 1993) or xylofuranose scaffold (Papageorgiou, C. et al., Bioorg.Med.Chem.Lett. 2, 135–140, 1992) or a benzodiazepinone scaffold (Papageorgiou, C. & Borer, X., Bioorg.Med.Chem.Lett. 6, 267–272, 1996) demonstrated low somatostatin receptor affinity. However, these structures are nonselective displaying higher affinities for both β2-adrenergic receptors and tachykinin receptors. Thus, there have been no reports in the literature on the successful development of a selective, competitive somatostatin receptor ligand of nonpeptide origin.

SUMMARY OF THE INVENTION

Accordingly, the present invention relates to a compound of general formula Ia or Ib

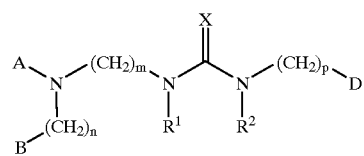

or

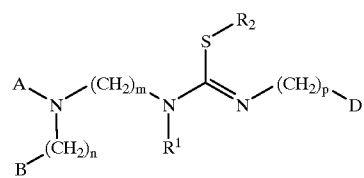

wherein
m is 2, 3, 4, 5 or 6, preferably 2, 3, 4 or 5,
n is 1, 2 or 3, preferably 1,
p is 1, 2, 3, 4, 5 or 6, preferably 2, 3 or 4,
$R^1$ and $R^2$ are independently hydrogen or $C_{1-6}$-alkyl optionally substituted with halogen, amino, hydroxy, alkoxy or aryl,
X is =S, =O, =NH, =NCOPh or =N(CN),
A is aryl, preferably pyridinyl, quinolinyl, isoquinolinyl, pyrimidinyl, pyrazinyl, pyridazinyl or triazinyl optionally substituted with one or more, preferably one or two halogen, amino, hydroxy, nitro, $C_{1-6}$-alkyl, $C_{1-6}$-alkoxy or aryl,
B is aryl, preferably phenyl, naphthyl, quinolinyl, isoquinolinyl, indolyl, thienyl, furanyl or pyridinyl optionally substituted with one or more, preferably one or two halogen, amino, hydroxy, $C_{1-6}$-alkyl, $C_{1-6}$-alkoxy or aryl,
D is aryl, preferably imidazolyl, pyridinyl, pyrimidinyl, piperazinyl, triazolyl, tetrazolyl, thiadiazolyl, isoxazolyl or oxadiazolyl optionally substituted with one or more, preferably one or two halogen, amino, hydroxy, $C_{1-6}$-alkyl, $C_{1-6}$-alkoxy or aryl; or amino, piperidinyl, pyrrolidinyl or morpholinyl, optionally substituted with $C_{1-6}$-alkyl or aryl, and the pharmaceutically acceptable salts thereof.

The compounds of formula Ia or Ib comprise any optical isomers thereof, in the form of separated, pure or partially purified optical isomers or racemic mixtures thereof.

In one embodiment of the compound of formula Ia, X is =S, =NH, =NCOPh, or =N—CN, preferably =S, =NH or =NCOPh.

In another embodiment of the compound of formula Ia or Ib, A is pyridinyl, e.g. pyridin-2-yl, pyridin-3-yl, quinolinyl, e.g. quinol-2-yl, isoquinolinyl, pyrimidinyl, e.g. pyrimidin-2-yl, pyrazinyl, pyridazinyl, e.g. pyridazin-2-yl, or triazinyl optionally substituted with one halogen, e.g. 5-bromo, amino, hydroxy, nitro, e.g. 5-nitro, $C_{1-6}$-alkyl $C_{1-6}$-alkoxy or aryl.

Preferably A is pyridinyl or quinolinyl optionally substituted with halogen, amino, hydroxy, nitro, $C_{1-6}$-alkyl, $C_{1-6}$-alkoxy or aryl, preferably pyridinyl, pyridinyl substituted with bromo or nitro, or quinolinyl.

In a further embodiment of the compound of formula Ia or Ib, B is phenyl, naphthyl, e.g. naphth-1-yl or naphth-2-yl, quinolinyl, isoquinolinyl, indolyl, thienyl, furanyl or pyridinyl optionally substituted with one or two halogen, e.g. 4-bromo or 3,4-dichloro, amino, hydroxy, $C_{1-6}$-alkyl, $C_{1-6}$-alkoxy or aryl.

Preferably B is phenyl or naphthyl optionally substituted with halogen, amino, hydroxy, nitro, $C_{1-6}$-alkyl, $C_{1-6}$-alkoxy or aryl, preferably phenyl substituted with bromo or two chloro, or naphthyl, e.g naphth-1-yl.

In a still further embodiment of the compound of formula Ia or Ib, D is amino, imidazolyl, e.g. 1H-imidazol-4-yl or imidazol-1-yl pyridinyl, e.g. pyridin-2-yl, pyrimidinyl, piperidinyl, pyrrolidinyl, e.g. pyrrolidin-1-yl, piperazinyl, pyridinylamino, pyrimidinylamino, piperidinylamino, pyrrolidinylamino, piperazinylamino, morpholinyl, e.g. morpholin-4-yl, triazolyl, tetrazolyl, thiadiazolyl, isoxazolyl or oxadiazolyl optionally substituted with one or two halogen, amino, hydroxy, $C_{1-6}$-alkyl, $C_{1-6}$-alkoxy or aryl.

Preferably D is imidazolyl, morpholinyl, pyrrolidinyl, amino or pyridinylamino optionally substituted with one or two halogen, amino, hydroxy, $C_{1-6}$-alkyl, $C_{1-6}$-alkoxy or aryl, preferably imidazolyl, morpholinyl, dimethylamino, pyrrolidinyl, pyridinylamino, amino or pyridinyl.

In a further embodiment of the compound of formula Ia or Ib, $R_1$ and $R_2$ are independently of each other hydrogen or $C_{1-6}$-alkyl, preferably hydrogen or methyl.

Whenever a heteroaryl or aryl is substituted such substitution(s) may be in any possible ring position, which may be recognized by the skilled person without any undue burden.

In another aspect the invention relates to somatostatin receptor ligands of nonpeptide origin which have affinity to the somatostatin receptor proteins selected from SST1, SST2, SST3, SST4 and SST5.

In an embodiment of the somatostatin receptor ligands of nonpeptide origin, said ligands have selective affinity to one or two of the somatostatin receptor proteins selected from SST1, SST2, SST3, SST4 and SST5.

In a further embodiment of the somatostatin receptor ligands of nonpeptide origin, said ligands have selective affinity to SST1.

In a still further embodiment of the somatostatin receptor ligands of nonpeptide origin, said ligands have selective affinity to SST2.

In a further embodiment of the somatostatin receptor ligands of nonpeptide origin, said ligands have selective affinity to SST3.

In a still further embodiment of the somatostatin receptor ligands of nonpeptide origin, said ligands have selective affinity to SST4.

In a further embodiment of the somatostatin receptor ligands of nonpeptide origin, said ligands have selective affinity to SST5.

In a still further embodiment of the somatostatin receptor ligands of nonpeptide origin, said ligands have selective affinity to SST1 and SST2, SST2 and SST3, SST3 and SST4, SST4 and SST5, SST1 and SST3, SST2 and SST4 or SST3 and SST5.

DETAILED DESCRIPTION OF THE INVENTION

Examples of specific compounds of the present invention are 1-(3-(N-(5-Bromopyridin-2-yl)-N-(3,4-dichlorobenzyl) amino)propyl)-3-(3-(1H-imidazol-4-yl)propyl)thiourea

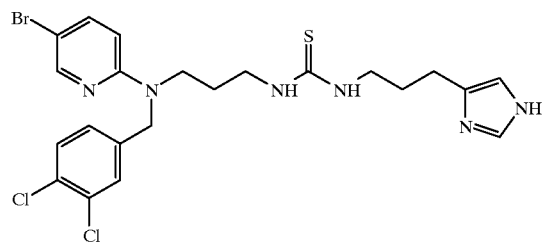

1-(3-(N-(4-Bromobenzyl)-N-(pyridin-2-yl)amino) propyl)-3-(3-(1H-imidazol-4-yl)propyl)thiourea

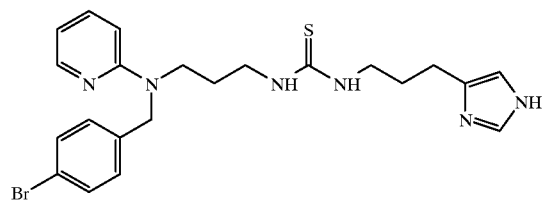

1-(4-Aminobutyl)-3-(3-(N-(5-bromopyridin-2-yl)-N-(3,4-dichlorobenzyl)amino)propyl)thiourea

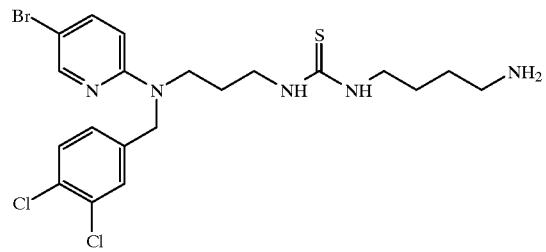

1-(3-(N-(5-Bromopyridin-2-yl)-N-(3,4-dichlorobenzyl)-amino)propyl)-3-(3-(N-(pyridin-2-yl)amino)propyl) thiourea

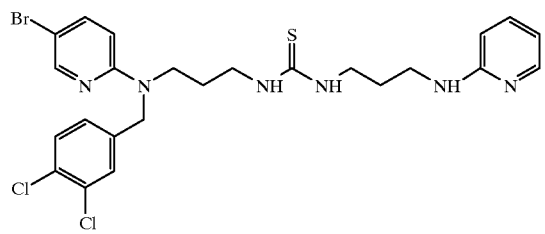

1-(3-(N-(4-Bromobenzyl)-N-(pyridin-2-yl)amino) propyl)-3-(3-(N,N-dimethylamino)propyl)thiourea

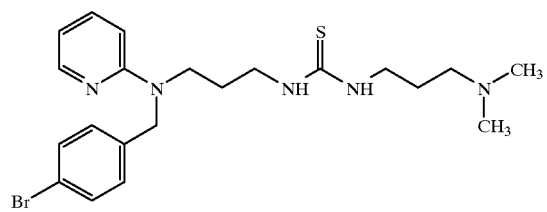

1-(3-(N-(4-Bromobenzyl)-N-(pyridin-2-yl)amino) propyl)-3-(3-(morpholin-4-yl)propyl)thiourea

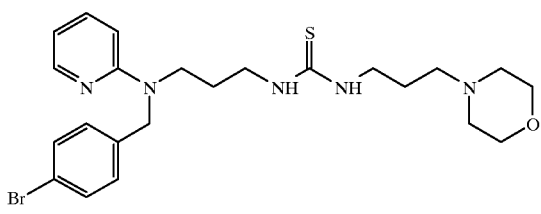

1-(3-(N-(4-Bromobenzyl)-N-(pyridin-2-yl)amino)
propyl)-3-(3-(imidazol-1-yl)propyl)thiourea

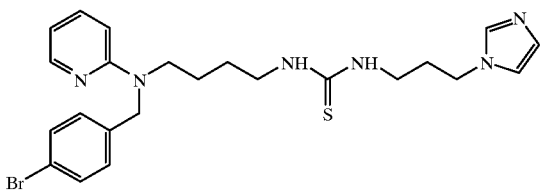

1-(4-(N-(4-Bromobenzyl)-N-(pyridin-2-yl)amino)butyl)-3-(3-(imidazol-1-yl)propyl)thiourea

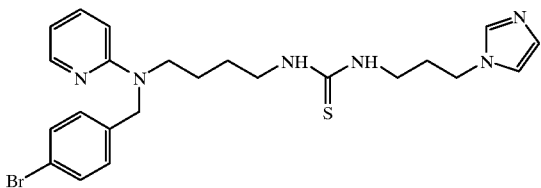

1-(4-(N-(3,4-Dichlorobenzyl)-N-(pyridin-2-yl)amino)
butyl)-3-(3-(imidazol-1-yl)propyl)thiourea

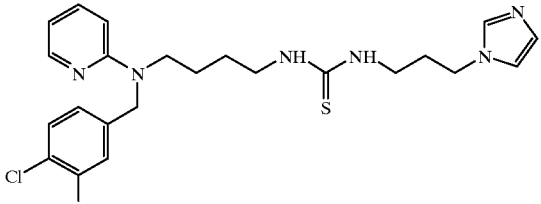

1-(3-(N-(5-Bromopyridin-2-yl)-N-(3,4-dichlorobenzyl)
amino)propyl)-3-(3-(imidazol-1-yl)propyl)thiourea

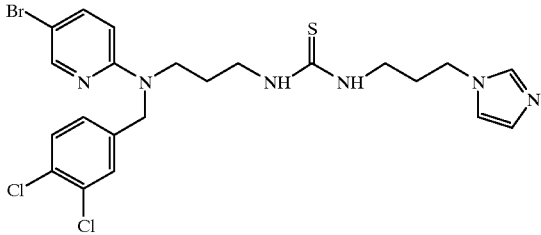

1-(4-(N-(5-Bromopyridin-2-yl)-N-(3,4-dichlorobenzyl)
amino)butyl)-3-(3-(imidazol-1-yl)propyl)thiourea

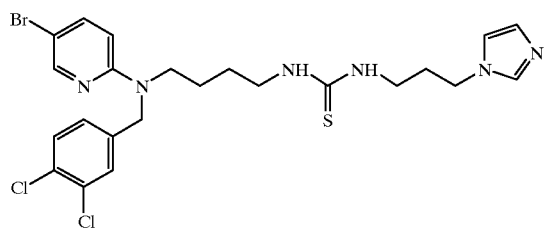

1-(3-(N-(4-Bromobenzyl)-N-(pyridin-2-yl)amino)
propyl)-3-(4-(N-(pyridin-2-yl)amino)propyl)thiourea

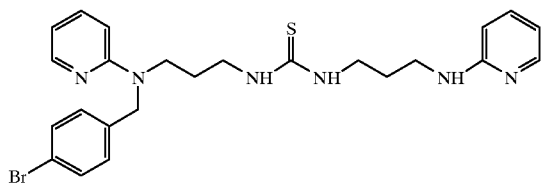

1-(4-(N-(5-Bromopyridin-2-yl)-N-(3,4-dichlorobenzyl)
amino)butyl)-3-(3-(1H-imidazol-4-yl)propyl)thiourea

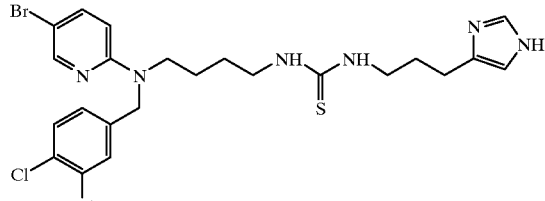

1-(5-(N-(5-Bromopyridin-2-yl)-N-(3,4-dichlorobenzyl)
amino)pentyl)-3-(3-(1H-imidazol-4-yl)propyl)thiourea

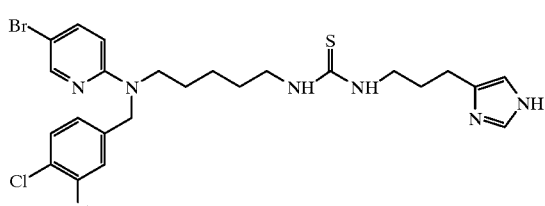

1-(4-(N-(5-Bromopyridin-2-yl)-N-(3,4-dichlorobenzyl)
amino)butyl)-3-(2-(1H-imidazol-4-yl)ethyl)thiourea

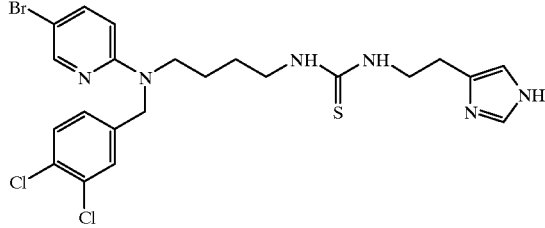

1-(2-(N-(5-Bromopyridin-2-yl)-N-(3,4-dichlorobenzyl)
amino)ethyl)-3-(2-(1H-imidazol-4-yl)ethyl)thiourea

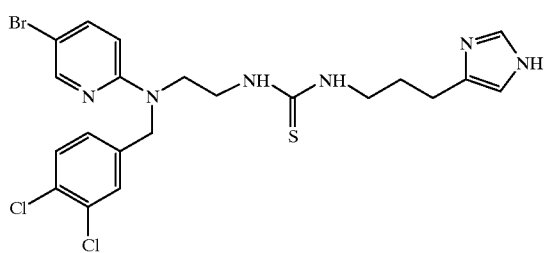

1-(2-(N-(5-Bromopyridin-2-yl)-N-(3,4-dichlorobenzyl)amino)ethyl)-3-(3-(1H-imidazol-4-yl)propyl)thiourea

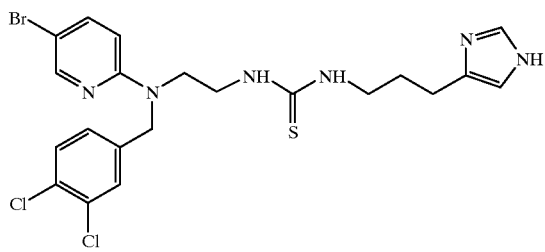

1-(3-(N-(5-Bromopyridin-2-yl)-N-((naphth-1-yl)methyl)-amino)propyl)-3-(3-(1H-imidazol-4-yl)propyl)thiourea

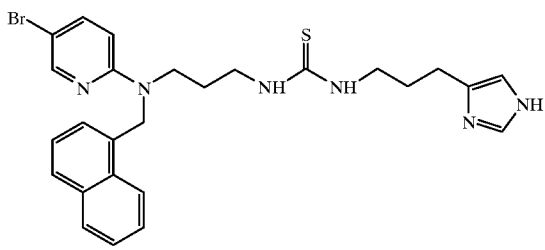

1-(4-Aminobutyl)-3-(3-(N-(5-bromopyridin-2-yl)-N-((naphth-1-yl)methyl)amino)propyl)thiourea

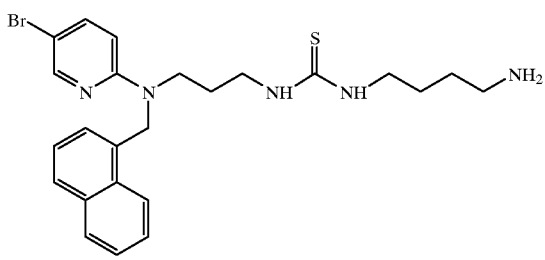

1-(2-(N-(5-Nitropyridin-2-yl)-N-(3,4-dichlorobenzyl)amino)ethyl)-3-(3-(1H-imidazol-4-yl)propyl)thiourea

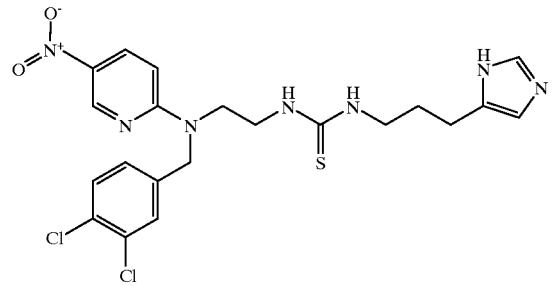

1-(2-(N-(5-Bromopyridin-2-yl)-N-(3,4-dichlorobenzyl)amino)ethyl)-3-(3-(pyrrolidin-1-yl)propyl)thiourea

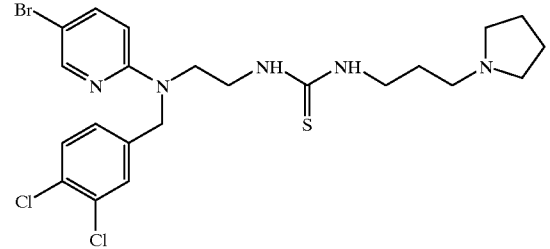

1-(2-(N-(5-Bromopyridin-2-yl)-N-(3,4-dichlorobenzyl)amino)ethyl)-3-(3-dimethylaminopropyl)thiourea

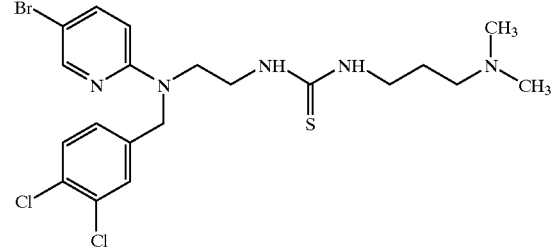

1-(3-(N-(5-Bromopyridin-2-yl)-N-(3,4-dichlorobenzyl)amino)propyl)-3-(4-(N-(pyridin-2-yl)amino)propyl)thiourea

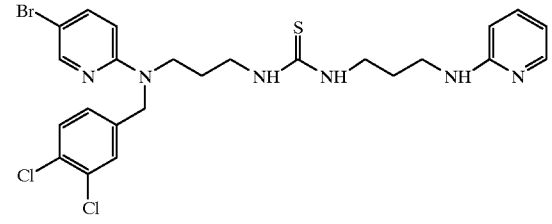

1-(4-Aminobutyl)-3-[3-[N-(5-bromopyrid-2-yl)]-[N-(3,4-dichlorobenzyl)]aminopropyl]thiourea

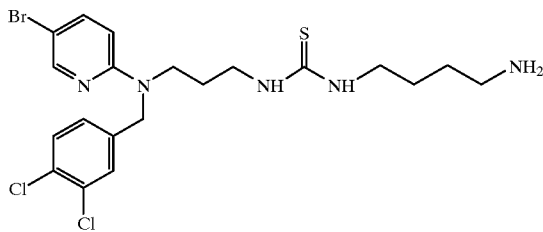

1-(3-(N-(5-Bromopyridin-2-yl)-N-(3,4-dichlorobenzyl)
amino)propyl)-3-(3-(pyrrolidin-1-yl)propyl)thiourea

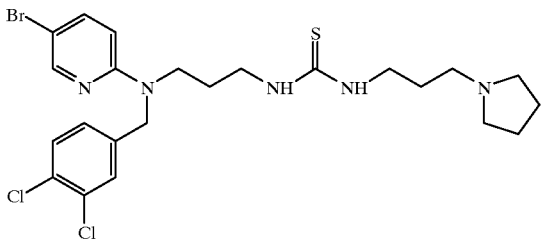

1-(3-(N-(5-Bromopyridin-2-yl)-N-(3,4-dichlorobenzyl)
amino)propyl)-3-(2-(pyrid-2-yl)ethyl)thiourea

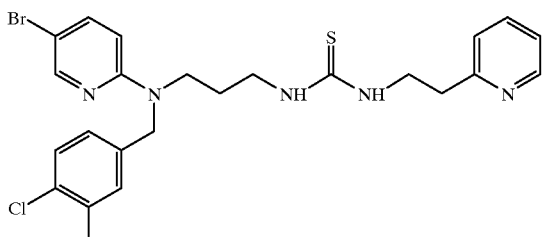

1-[3-[N-(4-Bromobenzyl)-N-(pyridin-2-yl)amino]
propyl]-3-[2-(1H-imidazol-4-yl)propyl]guanidine

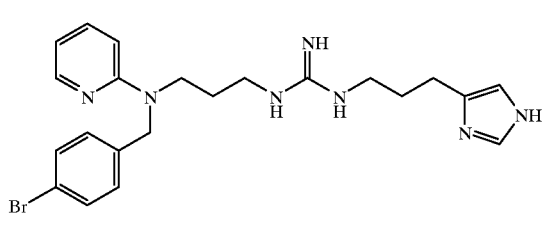

1-[3-[N-(4-Bromobenzyl)-N-(pyridin-2-yl)amino]
propyl]-3-[2-(1H-imidazol-4-yl)ethyl]guanidine

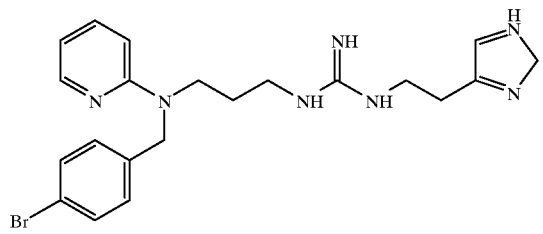

1-[3-[N-(4-Bromobenzyl)-N-(pyridazin-2-yl)amino]
propyl]-3-[3-(1H-imidazol-4-yl)propyl]guanidine

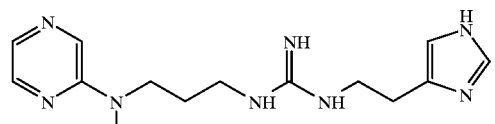

1-[3-[N-(4-Bromobenzyl)-N-(pyridin-3-yl)amino]
propyl]-3-[3-(1H-imidazol-4-yl)ethyl]guanidine

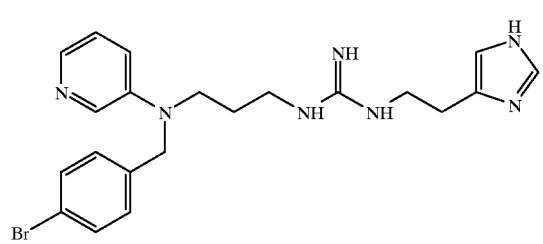

1-[3-[N-(4-Bromobenzyl)-N-(pyrimidin-2-yl)amino]
propyl]-3-[2-(1H-imidazol-4-yl)ethyl]guanidine

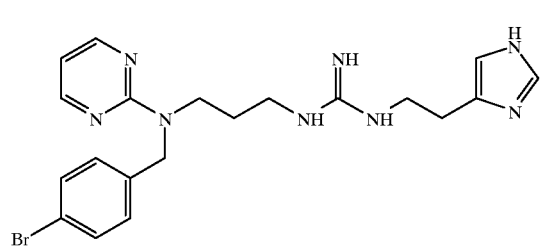

1-[3-[N-(4-Bromobenzyl)-N-(pyridin-2-yl)amino]
propyl]-3-[3-(imidazol-1-yl)propyl]guanidine

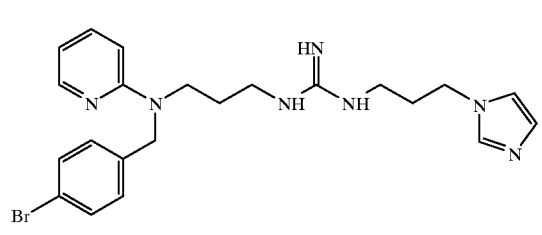

1-[3-[N-(4-Bromobenzyl)-N-(pyridin-2-yl)amino]
propyl]-3-[3-[N-(pyridin-2-yl)amino]propyl]guanidine

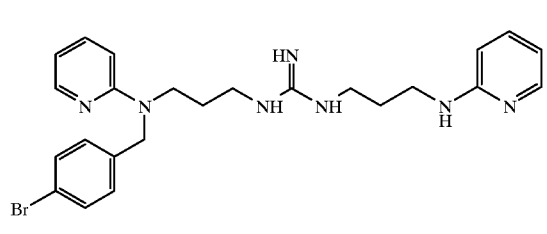

1-[3-[N-(4-Bromobenzyl)-N-(pyridin-2-yl)amino]
propyl]-3-[2-(pyridin-2-yl)ethyl]guanidine

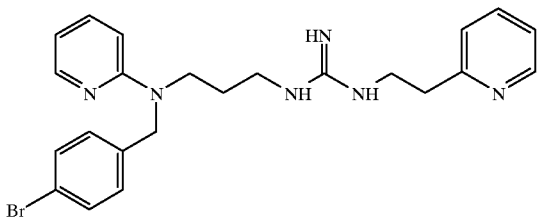

1-[3-[N-(4-Bromobenzyl)-N-(pyridin-2-yl)amino]
propyl]-3-[3-(morpholin-4-yl)propyl]guanidine

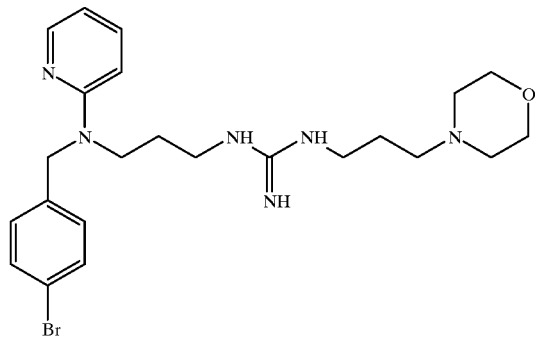

1-Methyl-1-[3-(N,N-dimethylamino)propyl]-3-[3-[N-(4-bromobenzyl)-N-(pyridin-2-yl)amino]propyl]guanidine

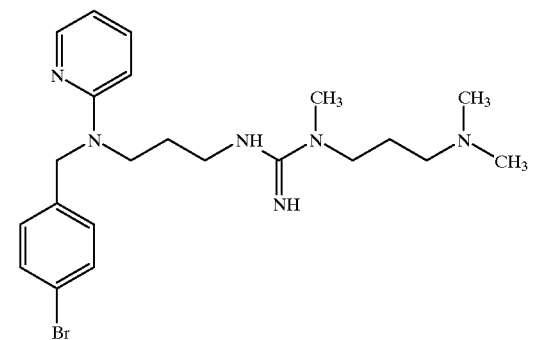

1-[3-[N-(4-bromobenzyl)-N-(quinol-2-yl)amino]-propyl]-2-Benzoyl-3-[3-(1H-imidazol-4-yl)propyl]guanidine

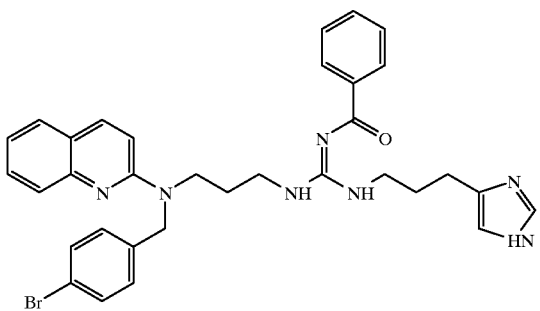

N1-[3-(Imidazol-4(5)-yl)propyl]-N2-[3-[N-(4-bromobenzyl)-N-(pyridin-2-yl)-amino]propyl]-S-methylisothiourea

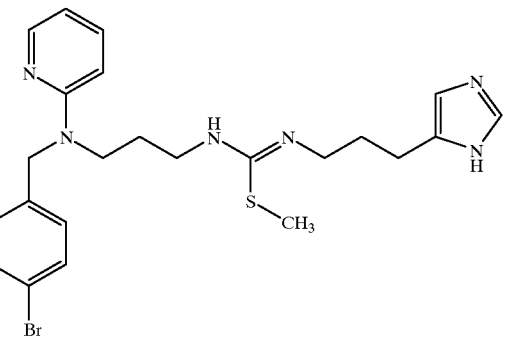

The compounds of the invention can be employed to mediate the biological effects of somatostatin agonists or antagonists. It is predicted that compounds of formula Ia or Ib exhibit an improved bioavalability because they contain no amide bonds susceptible to cleavage by proteolytic enzymes. The increased resistance to proteolytic degradation combined with the reduced size of the compounds of the invention in comparison with known somatostatin agonists and antagonists is expected to possess beneficial properties such as increased peroral absorption, increased biological half-life, lack of immunogenicity, and the ability to cross the blood-brain barrier compared to that of the compounds suggested in the prior literature.

Compounds of formula Ia or Ib are believed to be useful for the development of pharmaceutical, therapeutic, and diagnostic techniques. Accordingly, the invention also provides methods for producing a prophylactic or therapeutic responce in a mammal by administering to the mammal a pharmaceutically effective amount of one or more compounds of the invention. In accordance with preferred embodiments, the present invention provides methods for producing such responses by modulating the activity of mammalian somatostatin receptors by administering an effective amount of one or more compounds of the invention.

In the above structural formulas and throughout the present specification, the following terms have the indicated meanings:

The $C_{1-6}$-alkyl groups specified above are intended to include those alkyl groups of the designated length in either a linear or branched or cyclic configuration. Examples of linear alkyl are methyl, ethyl, propyl, butyl, pentyl, and hexyl. Examples of branched alkyl are isopropyl, sec-butyl, tert-butyl, isopentyl, and isohexyl. Examples of cyclic alkyl are $C_{3-6}$-cycloalkyl such as cyclopropyl, cyclobutyl, cyclopentyl and cyclohexyl.

The alkoxy groups, preferably $C_{1-6}$-alkoxy groups specified above are intended to include those alkoxy groups of the designated length in either a linear or branched or cyclic configuration. Examples of linear alkyloxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are $C_{3-6}$-cycloalkoxy such as cyclopropyloxy, cyclobutyloxy, cyclopentyloxy and cyclohexyloxy.

In the present context, the term "aryl" is intended to include aromatic rings, such as carbocyclic and heterocyclic aromatic rings selected from the group consisting of phenyl, naphthyl, thienyl, furyl, furanyl, pyridinyl, pyridyl, 1-H-tetrazol-5-yl, thiazolyl, imidazolyl, isoquinolinyl, indolyl, isoindolyl, piperidinyl, piperazinyl, pyridazinyl, pyrimidinyl, thiadiazolyl, pyrazolyl, oxadiazol, oxazolyl, isoxazolyl, thiopheneyl, quinolinyl, pyrazinyl, triazinyl, triazolyl, tetrazolyl or isothiazolyl, optionally substituted by one or more halogen, amino, hydroxy, carboxylic acid, carboxylic amide, nitrile, aldehyde, nitro, trihalogenomethyl, $C_{1-6}$-alkylketone, $C_{1-6}$-alkyl, $C_{1-6}$-alkoxy or aryl.

The term "halogen" is intended to include Chloro (Cl), Fluoro (F), Bromo (Br) and Iodo (I).

The compounds of the present invention may have one or more asymmetric centres and stereoisomers in the form of separated, pure or partially purified stereoisomers or racemic mixtures thereof are intended to be included in the scope of the invention.

General Method A
Reaction Scheme I

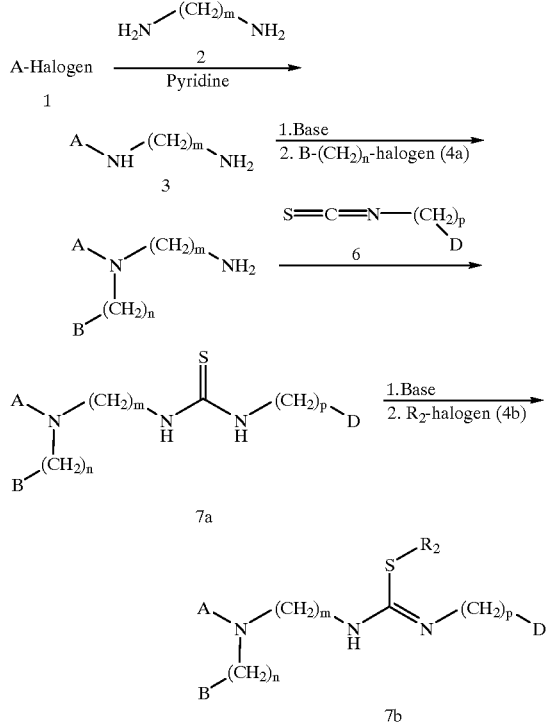

Compounds of formula Ia or formula Ib may be prepared as shown in reaction scheme I starting with an arylhalogenide 1 which may be reacted with a diaminoalkyl 2 in an appropriate solvent such as pyridine and under nitrogen at reflux for an appropriate time. The excess diaminoalkyl and solvent may be removed in vacuo and an apolar solvent such as tetrahydrofuran may be added to precipitate the diaminoalkyl salt. The intermediate 3 may be obtained by distillation or chromatography by methods known in the art.

The intermediate 3 may be alkylated with an arylalkylhalogenide 4a after treatment with a base such as sodium hydrid under conditions known in the art to give a 1,1-disubstituted primary amine 5. Then 5 in a solvent like tetrahydrofuran or ethanol may be reacted with an isothiocyanate 6, prepared as shown in scheme 2, stirred overnight and concentrated in vacuo to afford a crude product 7a. The isothiocyanate may be protected and deprotected according to methods described in the art (e.g. T. W. Greene, Protective Groups in Organic Synthesis, 2nd. edition, John Wiley and Sons, New York, 1991). The crude product 7a may be purified by methods known for those skilled in the art such as chromatography, to yield the final product 7a which is a compound of the general formula Ia. In the presence of a base such as sodium hydride, and an alkyl halide 4b the compound 7b which is a compound of the general formula Ib may be obtained.

Reaction Scheme II

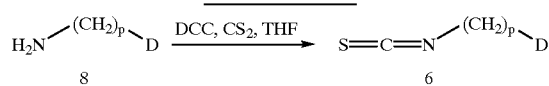

The isothiocyanate 6 as described in scheme I may be prepared from the appropriate protected primary amine 8 in a solvent like tetrahydrofuran and carbondisulfide in the presence of a reagent such as dicyclohexylcarbodiimide or other coupling reagents known in the literature under chilled conditions. The mixture may be stirred overnight and the solvent removed and the residue may be triturated with ether to remove dicyclohexylthiourea. The remaining product may be distilled under vacuum or chromatographed using technics known to those skilled in the art, to yield the isothiocyanate 6.

General Method B
Reaction Scheme III

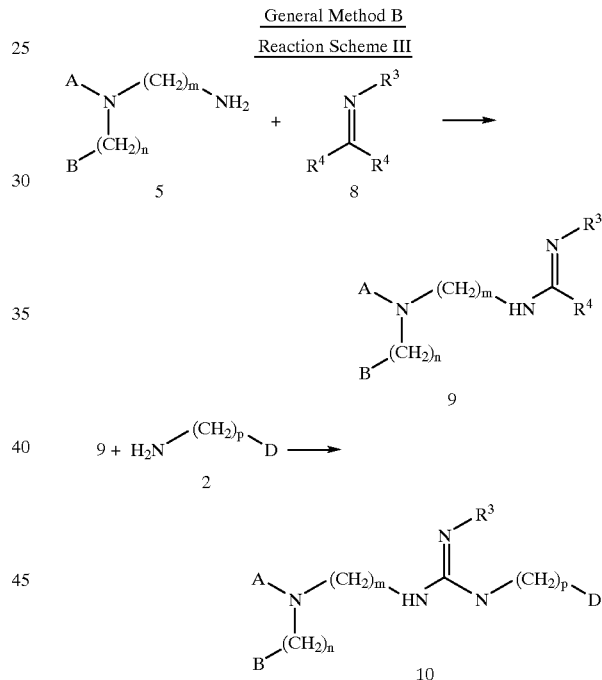

Compounds of formula Ia may be prepared as shown in reaction scheme III starting with an appropriate amine 5, prepared as described in reaction scheme I, and an activated imine 8 in which $R^3$ may be benzoyl(—COPh) or nitrile (—CN) and $R^4$ may be thiomethoxy (—SCH$_3$), phenoxy (—OPh) or cloride (—Cl) in an appropriate solvent such as dimethylformamide or tetrahydrofuran at an appropriate temperature for an appropriate time to give the intermediate 9. The intermediate 9 may further react with an amine 2 in an appropriate solvent such as pyridine with or without a catalyst e.g. silver salts (e.g. AgNO$_3$) at an appropriate temperature for an appropriate time to form the product 10 which is a compound of the general formula Ia.

When the compound 10 (in which $R^3$ is an activating group such as benzoyl or nitrile) is treated with 1.5 M aqueous hydrogen chloride for an appropriate time at an appropriate temperature the compound 10 (in which $R^3$ is hydrogen) may be formed which is a compound of the general formula Ia.

The intermediates in reaction scheme III may be protected and deprotected according to methods described in the art (e.g. T. W. Greene, Protective Groups in Organic Synthesis, 2nd. edition, John Wiley and Sons, New York, 1991).

The guanidine derivatives and their salts thus obtained can be isolated and purified by methods which are known by those skilled in the art.

Pharmacology

Compounds of the invention are preferred to the extent that they selectively and effectively are bound by somatostatin receptor subtypes permanently expressed in eukariotic cell lines. It will be recognized that the degree to which a compound is bound by a receptor is known as its binding affinity. The affinity of a compound is commonly expressed as the inhibitory concentration at which the compound is able to displace 50% of another compound already bound to the receptor ($IC_{50}$). In the case of ligand-binding studies at somatostatin receptors, the compound that is displaced is a radioactive agonist, e.g. $^{125}I$-$Tyr^{11}$-SRIF-14, at the receptor. It is preferred in accordance with the present invention that a compound possess a clinically effective $IC_{50}$ in at least one mammal; that is, it should possess an $IC_{50}$ which is low enough to inhibit binding of radiolabelled agonist to somatostatin receptors while causing a minimum of unacceptable side effects in the mammal. As will be recognized, clinically effective concentrations vary depending on a number of factors, such as the pharmacokinetic characteristics and stability of the compound under study and thus must be determined empirically for each compound and each factor. In general, it is desired that the potency of a compound of the invention be as great as possible, preferable greater than or equal to the native somatostatin. Compounds displacing radiolabelled agonist at somatostatin receptors could belong to one of two classes, either agonists or antagonists. Simple ligand-binding studies will not distinguish between these two classes. All five somatostatin receptor subtypes (ie. SST1, SST2, SST3, SST4 and SST5) have been shown to inhibit the activity of adenylyl cyclase via the G protein subunit $G_1$ (Patel, Y. C. et al. Biochem. Biophys.Res.Commun., 198:605–612, 1994). By direct activation of adenylyl cyclase by forskolin the inhibitory action of somatostatin agonists could be employed. Compounds specifically reversing the inhibitory action of SRIF on cyclic AMP accumulation will be termed somatostatin receptor antagonists.

Those skilled in the art will appreciate that a wide variety of prophylactic, diagnostic, and therapeutic treatments may be prepared from the compounds and compositions of this invention, due to agonism or antagonism at somatostatin receptors. For example, by administering an effective amount of compound, prophylactic or therapeutic responses can be produced in a human or some other type mammal. Preferred responses are modulation of glucagon and insulin secretion to treat type I and type II diabetes; inhibition of cell proliferation and growth to treat various endocrine and exocrine tumours; modulation of growth hormone secretion to treat dwarfism, acromegaly, and other growth abnormalities; modulation of immune responses to treat autoimmune diseases, rheumatoid arthritis, and other inflammations; modulation of neuronal activity to treat diseases related to the central nervous system, i.e. pain, anxiety, memory disorders, affective disorders, and Alzheimers disease; modulation of intestinal water uptake to treat congestion and diarrhea; inhibition of arterial smooth muscle cell proliferation to treat restenosis and arteriosclerosis; inhibition of airway mucous secretion to treat asthma and mucoviscidosis; modulation of lipid metabolism and regulation of energy balance to treat obesity; inhibition of acid secretion to treat ulcer; inhibition of pancreatic secretions to treat acute pancreatitis. It will be appreciated that the production of prophylactic or therapeutic responses includes the initiation or enhancement of desirable responses, as well as the cessation or suppression of undesirable responses.

As can be seen, the present invention provides a variety of compounds which effectively and selectively are bound to somatostatin receptors. The compounds are capable of forming pharmaceutically acceptable salts with various inorganic and organic acids, and such salts are also within the scope of this invention. Examples of such salts are acid addition salts including acetate, adipate, benzoate, benzenesulfonate, bisulfate, butyrate, citrate, camphorate, camphorsulfonate, ethanesulfonate, fumarate, hemisulfate, heptanoate, hexanoate, hydrochloride, hydrobromide, hydroiodide, lactate, maleate, methanesulfonate, 2-naphthalenesulfonate, nitrate, oxalate, pamoate, persulfate, picrate, pivalate, propionate, succinate, sulfate, tartrate, tosylate, and undecanoate. The salts may be formed by conventional means, such as by reacting the free base form of the product with one or more equivalents of the appropriate acid in a solvent or medium in which the salt is insoluble, or in a solvent such as water, which is later removed in vacuo or by freeze drying. The salts also may be formed by exchanging the anions of an existing salt for another anion on a suitable ion exchange resin.

In another aspect, the present invention relates to a pharmaceutical composition comprising, as an active ingredient, a compound of the general formula Ia or formula Ib or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula Ia or formula Ib dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage.

The dosage of the compounds according to this invention is suitably 1–500 mg/day, e.g. about 100 mg per dose, when administered to patients, e.g. humans, as a drug.

It has been demonstrated that compounds of the general formula Ia or formula Ib possess the ability to bind to human somatostatin receptors. The compounds may therefor be used in the treatment of conditions which require high somatostatin receptor affinity.

Thus, in a particular aspect, the present invention relates to a pharmaceutical composition for binding to somatostatin receptors, the composition comprising, as an active ingredient, a compound of the general formula Ia or formula Ib or a pharmaceutically acceptable salt therof together with a pharmaceutically acceptable carrier or diluent.

In a further aspect, the present invention relates to a method of binding to somatostatin receptors, the method comprising administering to a subject in need thereof an effective amount of a compound of the general formula Ia or formula Ib or a pharmaceutically acceptable salt thereof.

In a still further aspect, the present invention relates to the use of a compound of the general formula Ia or formula Ib or a pharmaceutically acceptable thereof for the preparation of a medicament for binding to the somatostatin receptors.

Those skilled in the art will appreciate that a wide variety of prophylactic, diagnostic, and therapeutic treatments may be prepared from the synthetic compounds and compositions of the invention, due in large part to the competition—that is, agonism or antagonism—of these moieties with the naturally-occuring SRIF or SRIF-28. For example, by administering an effective amount of a compound of the invention, prophylactic or therapeutic responses can be produced in a human or some other type mammal. Preferred responses are produced by modulating—that is, increasing, decreasing or otherwise modifying—the activity of at least one somatostatin receptor subtype (ie. SST1, SST2, SST3, SST4 and SST5). It will be appreciated that the production of prophylactic or therapeutic responses includes the initiation or enhancement of desirable responses, as well as the cessation or suppression of undesirable responses.

The compounds of formula Ia or formula Ib may be used in the treatment of disorders with an aetiology comprising or associated with excess GH-secretion, gastrointestinal disorders, malignant cell proliferative diseases, angiogenesis, or in prevention or combating graft vessel diseases, restenosis and vascular occlusion following vascular injury.

The compounds of formula Ia or formula Ib may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

Optionally, the pharmaceutical composition of the invention may comprise a compound of formula Ia or formula Ib combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

EXAMPLES

The process for preparing compounds of formula Ia or formula Ib and preparations containing them is further illustrated in the following examples, which however, are not to be construed as limiting.

The structures of the compounds are confirmed by either elemental analysis (MA) nuclear magnetic resonance (NMR) or mass spectrometry (MS). NMR shifts (d) are given in parts per million (ppm) and only selected peaks are given. m.p. is melting point and is given in ° C. and is not corrected. Column chromatography was carried out using the technique described by W. C. Still at al, J. Org. Chem. 1978, 43, 2923–2925 on Merck silica gel 60 (Art 9385). Compounds used as starting materials are either known compounds or compounds which can readily be prepared by methods known per se.

| Abbrevations | |
|---|---|
| TLC: | thin layer chromatography |
| DMSO: | dimethylsulfoxide |
| min: | minutes |
| h: | hours |

HPLC-Analysis:
Method A.

The RP-HPLC analysis was performed using UV detection at 254 nm and a Lichrosorp RP-18 5 mM column, which was eluted at 1 ml/minute. The column was equilibrated with 20% acetonitrile in a buffer consisting of 0.1M ammonium sulfate, which was adjusted to pH 2.5 with 4M sulfuric acid and eluted by a gradient of 20% to 80% acetonitrile in the same buffer over 30 minutes. The gradient was then extended to 100% acetonitrile over 5 minutes followed by isocratic elution with 100% acetonitrile for 6 minutes.

Biological Assays

The affinity of somatostatin receptor ligands of nonpeptide origin according to the invention (including the compounds covered by formula Ia and Ib) to the somatostatin receptor proteins selected from SST1, SST2, SST3, SST4 and SST5, may be detected using the assays described below. The skilled person will know which adjustments/ modifications to make in order to screen for specific ligands having affinity to one or more of the SST receptor subtypes 1–5. Moreover, in order to screen large compound libraries to find the present ligands, conventional techniques (see e.g. Amersham™ SPA Technology) known to the skilled person may be used to modify the assays. One way of producing the present ligands is to provide a compound library of nonpeptide origin using conventional techniques (see e.g. Combinatorial chemistry in the discovery and development of drugs. Doyle, P. M., Journal Of Chemical Technology And Biotechnology (1995) Vol. 64, 317–24) well-known to the skilled person, and screen for such ligands using the assays described below optionally with modifications, thereby providing somatostatin receptor ligands according to the invention.

Cell Lines Expressing SST Receptor Subtypes:

BHK cells (tk- ts13, ATCC CRL# 1632) and HEK 293 cells (ATCC CRL# 1573) were grown to 20–40% confluency in a tissue culture dish in Dulbeccos Modified Eagle Medium (DMEM) containing 1% penicillin/streptomycin, 10% foetal bovine serum, and 1% Glutamax™. Prior to transfection, the cells were washed twice with calcium-free PBS after which 20 ml of serum-free DMEM was added to the cells.

Transfection was carried out as described previously (product description: Lipofectamin, Gibco BRL cat. no. 18324-012). Briefly, 10 μg of cDNA encoding a SST receptor subtype inserted into the mammalian expression vector pcDNA3 (Invitrogen) was diluted in 300 μl of sterile water. 30 μg of Lipofectamin was diluted in 300 μl of sterile water. The cDNA and Lipofectamin solutions were mixed and left at room temperature for 15 minutes. The Lipofectamin/cDNA mixture was added drop-wise to the cells (HEK 293 cells for $SST_2$, BHK for the other receptor subtypes) while gently swirling the plates. The cells were then incubated for 16–24 hours, after which the medium was replaced with standard medium containing 1 mg/ml Geneticin (G-418 sulfate). Resistant colonies appearing after 1–2 weeks were isolated and propagated for further characterization.

Binding Assay:

Cells expressing individual SST receptor subtypes were resuspended in buffer (50 mM Tris-HCl (pH 7.4), 1 mM EGTA, 5 mM $MgCl_2$), and homogenised. Membranes were washed twice in buffer by homogenisation and centrifugation. Final membrane pellets were resuspended at a protein concentration of 125 μg/ml in buffer. Binding assays using 75 pM $^{25}I$-$Tyr^{11}$-SRIF (Amersham, IM-161) were done in duplicates in minisorb polypropylene tubes in a volume of 250 μl. The assays were incubated at 30–37° C. for 30–90 min depending on receptor subtype. Binding was terminated by filtration through Whatman GF/B glass fiber filters pre-soaked for 4 hrs. in 0.5% polyethyleneimine and 0.1% BSA. Filters were washed three times with 5 ml ice-cold 0.9% saline and counted in a Packard Cobra II Gamma Counter.

Functional Assay:

Cells expressing human SST receptors were seeded in 24-well tissue culture multi-dishes at 200,000 cells/well and grown for 16–20 hours. The medium was removed, and fresh DMEM medium, supplemented with 1) 1 mM 3-isobutyl-1-methylxanthine (IBMX), 2) 10 μm forskolin or medium, and 3) medium, SRIF, SST analogue, or compound was added. The plates were incubated for 15–30 min at 37° C., the reaction medium removed and the cells lysed with 0.1 M sodium hydroxide. Following neutralisation with 0.1 M hydrochloric acid an aliquot was removed for cAMP determination using Amersham SPA RIA (RPA 538).

Example 1

1-(3-(N-(4-Bromobenzyl)-N-(pyridin-2-yl)amino) propyl)-3-(3-(1H-imidazol-4-yl)propyl)thiourea dihydrochloride

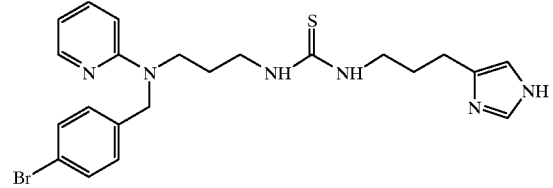

To a solution of propane-1,3-diamine (310 ml, 3.63 mol) in dry pyridine (75 ml) kept under an atmosphere of nitrogen 2-bromopyridine (70 ml, 0.73 mol) was added. The reaction mixture was heated at reflux for 18 h, cooled and the volatiles evaporated in vacuo. To the residue was added tetrahydrofuran (1 l) and the precipitate was filtered off and washed with tetrahydrofuran (0.5 l). The solvent was evaporated in vacuo and the residue purified by distillation at 95–97° C. and $2\times10^{-2}$ mbar affording 83.37 g (76%) of N-(pyridin-2-yl)propane-1,3-diamine.

$^1$H NMR (200 MHz, DMSO-$d_6$) d 1.20 (bs, 2H, $NH_2$), 1.74 (p, 2H), 2.82 (t, 2H), 3.34 (q, 2H, $CH_2$—NH), 4.86 (bs, 1H, NH), 6.35 (dt, 1H), 6.51 (ddd, 1H), 7.37 (ddd, 1H), 8.04 (ddd,1H).

To a mixture of sodium hydride (5.86 g, 60% dispersion in mineral oil, 0.1415 mol) in dry dimethylsulfoxide (250 ml) was slowly added a solution of N-(pyridin-2-yl)propane-1,3-diamine (20 g, 0.1323 mol) in dry dimethylsulfoxide (50 ml) at room temperature under an atmosphere of nitrogen. The reaction mixture was stirred until gas evolution was ceased. A solution of 4-bromobenzylbromide (36.09 g, 0.1415 mol) in dry dimethylsulfoxide (100 ml) was slowly added at room temperature. The reaction mixture was stirred for 48 h at room temperature. The reaction mixture was poured onto ice water (500 ml) and extracted with ethyl acetate (3×250 ml). The combined organic extracts were washed with water (3×150 ml), dried ($MgSO_4$), filtered and the solvent evaporated in vacuo. The residue (40.56 g) was washed with n-heptane (30 ml) which afforded 36.77 g of crude N-(4-bromobenzyl)-N-(pyridin-2-yl)propane-1,3-diamine. 20 g crude product was purified by column chromatography on silica gel (900 ml) using dichloremethane/methanol/triethylamine 9:0.5:0.5 as eluent affording 13.75 g (70%) of N-(4-bromobenzyl)-N-(pyridin-2-yl)propane-1,3-diamine as an oil.

$^1$H NMR (200 MHz, $CDCl_3$) d 1.64 (s, 2H, $NH_2$), 1.74 (t, 2H), 2.72 (t, 2H), 3.60 (t, 2H, $CH_2$—N), 4.67 (s, 2H, $CH_2$—Ph), 6.41 (d, 1H), 6.53 (dd, 1H), 7.07 (d, 2H), 7.33–7.41 (m, 3H), 8.13 (dt, 1H).

To a solution of N,N-dicyclohexylcarbodiimide (2.08 g, 10 mmol) in dry tetrahydrofuran (20 ml) was slowly added at −10° C. a solution of N-(4-bromobenzyl)-N-(pyridin-2-yl)-propane-1,3-diamine (3.20 g, 10 mmol) and carbondisulfide (4.3 ml, 70 mmol) in dry tetrahydrofuran (20 ml) under an atmosphere of nitrogen. The mixture was stirred at −10° C. for 3 h and for 48 h at room temperature. The reaction mixture was filtered and the solvent evaporated in vacuo. The residue (5.29 g) was extracted with diethyl ether (3×20 ml) and the combined organic extracts were evaporated in vacuo affording 3.2 g (88%) of N-(4-bromobenzyl)-N-(3-isothiocyanatopropyl)-N-(pyridin-2-yl)amine as an oil.

TLC: $R_f$=0.72 (SiO$_2$; ethyl acetate/n-heptan=1:1).

$^1$H NMR (200 MHz, CDCl$_3$) d 2.00 (q, 2H), 3.57 (t, 2H), 3.68 (t, 2H), 4.66 (s, 2H), 6.41 (d, 1H), 6.58 (dd, 1H), 7.07 (d, 2H), 7.35–7.43 (m, 3H), 8.15 (dd, 1H).

N-(4-bromobenzyl)-N-(3-isothiocyanatopropyl)-N-(pyridin-2-yl)amine(1 g, 2.76 mmol) and 3-(1-triphenylmethylimidazol-4-yl)propylamine (1.014 g, 2.76 mmol) were dissolved in chloroform (10 ml) and heated at reflux for 4 h. The solvent was removed by evaporation in vacuo and the residue (3.09 g) purified by column chromatography on silica gel (400 ml) using ethyl acetate/methanol/triethylamine 9:0.5:0.5 as eluent affording 1.59 g (80%) of pure 1-[3-(1-triphenylmethylimidazol-4-yl)propyl]-3-[3-[N-(4-bromobenzyl)-N-(pyridin-2-yl)amino]propyl]thiourea.

TLC: $R_f$=0.59 (SiO$_2$; ethyl acetate/methanol/triethylamine=9:0.5:0.5).

$^1$H NMR (200 MHz, CDCl$_3$) d 1.90 (m, 6H), 2.62 (t, 2H), 3.44–3.68 (m, 6H), 4.55 (s, 2H, CH$_2$—Ph), 6.33 (d, 1H), 6.49 (dd, 1H), 6.56 (s, 1H), 6.98–7.11 (m, 9H), 7.39 (m, 11H), 8.06 (d, 1H).

To a solution of the above thiourea (1.59 g, 2.215 mmol) in ethanol (50 ml), 1 N hydrochloric acid (16 ml) was added and the reaction mixture was heated to 50° C. for 10 h. The cooled reaction mixture was washed with diethyl ether (3×30 ml) and the aqueous phase evaporated in vacuo. The residue was extracted with absolute ethanol (3×20 ml) and evaporated in vacuo followed by drying in vacuo affording 1.23 g (99%) of the title compound as an amorphous powder.

$^1$H NMR (200 MHz, MeOD-d$_3$) d 2.0 (m, 4H), 2.77 (t, 2H), 3.57 (m, 4H), 3.76 (t, 2H, 4.90 (s, 2H, CH$_2$—Ph), 6.99 (t, 1H), 7.19 (d, 2H), 7.26 (d, 1H), 7.36 (s, 1H), 7.50 (d, 2H), 7.94 (d, 1H), 8.02 (dd, 1H), 8.78 (d, 1H).

Example 2

1-(3-(N-(4-Bromobenzyl)-N-(pyridin-2-yl)amino)propyl)-3-(3-(morpholin-4-yl)propyl)thiourea

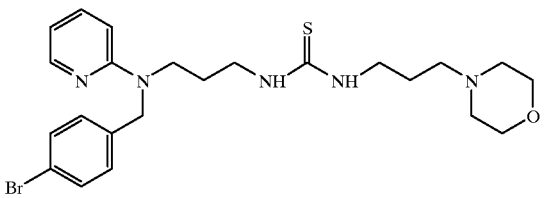

To a solution of N-(4-bromobenzyl)-N-(pyridin-2-yl)propane-1,3-diamine (1.0 g, 3.123 mmol) in chloroform (40 ml) was added 3-morpholinopropyl isothiocyanate (593 mg, 3.123 mmol) and the reaction mixture was stirred for 20 h at reflux temperature. To the reaction mixture was added 10 drops of 3-morpholinopropyl isothiocyanate and the reaction mixture was stirred for an additional 4 h at reflux temperature. The volatiles were evaporated in vacuo and the residue (2.05 g) was dissolved in ethyl acetate (20 ml) and left over night at room temperature. The precipitate was filtered off and washed with ethyl acetate and dried affording 1.20 g (76%) of the title compound as a solid.

TLC: $R_f$=0.39 (SiO$_2$; Ethyl acetate/Methanol/Triethylamine=90:5:5)

M.p. 121–123° C.

HPLC retention time=6.68 minutes (5 mM C18 4×250 mm column, eluting with 25% acetonitrile/0.1 N aqueous ammonium sulphate, pH=2.5, at room temperature)

$^1$H-NMR (200 MHz, CDCl$_3$) d 1.84 (m, 4H), 2.49 (m, 6H), 3.53 (m, 4H), 3.71 (m, 6H), 4.56 (s, 2H, CH$_2$—Ph), 6.36 (d, 1H), 6.57 (m, 1H), 7.04 (d, 1H), 7.22 (bs, 1H), 7.32–7.45 (m, 3H), 7.91 (bs, 1H), 8.15 (d, 1H).

Example 3

1-(3-(N-(4-Bromobenzyl)-N-(pyridin-2-yl)amino)propyl)-3-(3-N,N-dimethylaminopropyl)thiourea

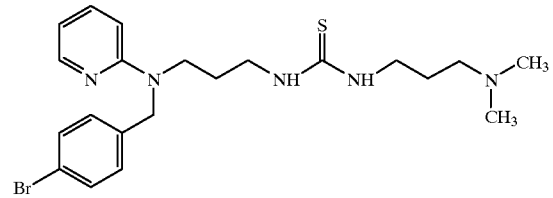

To a solution of N-(4-bromobenzyl)-N-(pyridin-2-yl)propane-1,3-diamine (1.0 g, 3.123 mmol) in chloroform (40 ml) was added 3-(dimethylamino)propyl isothiocyanate (460 mg, 3.123 mmol) and the reaction mixture was stirred for 5 h at reflux temperature. The volatiles were evaporated in vacuo and the residue (1.69 g) was purified by column chromatography on silica gel (180 ml) using ethyl acetate/methanol/triethylamine 7:2.5:0.5 as eluent affording (1.41 g) of a syrup which was crystallised from n-heptane affording 1.23 g (85%) of the title compound as a solid.

TLC: $R_f$=0.39 (SiO$_2$; Ethyl acetate/Methanol/Triethylamine=70:25:5)

M.p. 79–81° C.

HPLC retention time=6.09 minutes (5 mM C18 4×250 mm column, eluting with 25% acetonitrile/0.1 N aqueous ammonium sulphate, pH=2.5, at room temperature)

$^1$H-NMR (400 MHz, CDCl$_3$) d 1.72 (p, 2H), 1.84 (p, 2H), 2.19 (s, 6H), 2.40 (t, 2H), 3.48 (bs, 4H), 3.68 (t, 2H), 4.59 (s, 2H, CH$_2$—Ph), 6.37 (d, 1H), 6.56 (dd, 1H), 7.04 (d, 2H), 7.38 (m, 3H), 8.17 (bd, 1H).

Example 4

1-[3-[N-(4-bromobenzyl)-N-(quinolin-2-yl)amino]propyl]-2-Benzoyl-3-[3-(1H-imidazol-4-yl)propyl]guanidine

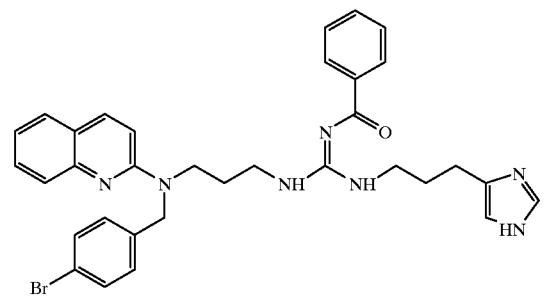

To a solution of propane-1,3-diamine (65.1 ml, 0.764 mol) in dry pyridine (25 ml) kept under an atmosphere of nitrogen 2-chloro-quinoline (25 g, 0.153 mol) was added. The reaction mixture was heated at reflux temperature for 18 h. To the cooled reaction mixture was added tetrahydrofuran (100 ml) and the precipitate was filtered off and washed with tetrahydrofuran (2×50 ml). The solvent was evaporated in vacuo and the residue purified by distillation at 154° C. and 2.5×10⁻² mbar affording 25.34 g (82%) of N-(quinolin-2-yl)propane-1,3-diamine as a crystallising oil.

¹H NMR (200 MHz, CDCl₃) d 1.37 (bs, 2H, NH₂), 1.77 (p, 2H), 2.83 (t, 2H), 3.59 (q, 2H, CH₂—NH), 5.22 (bs, 1H, NH), 6.59 (d, 1H), 7.17 (dt, 1H), 7.49 (m, 2H), 7.66 (d, 1H), 7.76 (d, 1H).

To a mixture of sodium hydride (2.64 g, 60% dispersion in mineral oil, 63.79 mmol) in dry dimethylsulfoxide (100 ml) was slowly added a solution of N-(quinolin-2-yl)propane-1,3-diamine (12 g, 56.62 mmol) in dry dimethylsulfoxide (25 ml) at room temperature under an atmosphere of nitrogen. The reaction mixture was stirred until gas evolution was ceased. To the resulting mixture a solution of 4-bromobenzylbromide (16.27 g, 63.79 mmol) in dry dimethylsulfoxide (50 ml) was slowly added at room temperature. The reaction mixture was stirred for 4 days at room temperature poured on to ice water (800 ml) and extracted with ethyl acetate (5×150 ml). The combined organic extracts were washed with water (4×150 ml), dried (MgSO₄), filtered and the solvent evaporated in vacuo. The residue (22.27 g) was washed with n-heptane (30 ml) which afforded 20.41 g of crude N-(4-bromobenzyl)-N-(quinolin-2-yl)propane-1,3-diamine which was purified by column chromatography on silica gel (900 ml) using a mixture of dichloromethane/methanol/triethylamine 9:0.5:0.5 as eluent affording 13.9 g (63%) of N-(4-bromobenzyl)-N-(quinolin-2-yl)propane-1,3-diamine as an oil.

¹H NMR (200 MHz, CDCl₃) d 1.76 (m, 4H), 2.74 (t, 2H), 3.78 (t, 2H), 4.80 (s, 2H), 6.77 (d, 1H), 7.16 (m, 3H), 7.41 (d, 2H), 7.55 (m, 2H), 7.67 (d, 1H), 7.81 (d, 1H).

To a solution of the above amine (8.0 g, 21.604 mmol) in dichloromethane (100 ml) was added N-benzoyl-dimethyldithioimidocarbonate (4.87 g, 21.604 mmol) and the reaction mixture was stirred at room temperature for 20 h. The solvent was evaporated in vacuo and the residue was purified by column chromatography on silica gel (900 ml) using a mixture of ethyl acetate and heptane 1:2 as eluent affording 10.92 g (92%) of 1-benzoyl-3-[3-[N-(4-bromobenzyl)-N-(quinolin-2-yl)amino]-propyl]-2-methylisothiourea.

To a solution of the above isothiourea (5.0 g, 9.133 mmol) in dry pyridine (70 ml) was added 3-(1H-imidazol-4-yl)propyl amine (1.26 g, 10.05 mmol) and the resulting mixture was stirred at reflux temperature for 10 h followed by stirring at room temperature for 48 h. The solvent was evaporated in vacuo and the residue was purified by column chromatography on silica gel (600 ml) using a mixture of dichloromethane/methanol/triethylamine 9:0.5:0.5 as eluent affording 3.31 g (58%) of the title compound as an amorphous solid.

¹H NMR (200 MHz, CDCl₃) d 1.84 (bs, 2H), 2.01 (m, 2H), 2.59 (m, 2H), 3.24–3.70 (m, 4H), 3.80 (t, 2H), 4.78 (s, 2H), 6.69 (s, 1H), 6.76 (d, 1H), 7.09 (d, 2H), 7.22 (dt, 2H), 7.29–7.80 (m, 9H), 8.18 (d, 2H).

HPLC retention time=26.10 minutes (5 mM C18 4×250 mm column, eluting with a gradient of 15% acetonitrile/0.1 N aqueous ammonium sulphate to 25% acetonitrile/0.1 N aqueous ammonium sulphate, pH=2.5, over 10 minutes at room temperature).

Example 5

1-[3-[N-(4-Bromo-benzyl)-N-(quinolin-2-yl)amino]-propyl]-3-[3-(1H-imidazol-4-yl)propyl]guanidine trihydrochloride

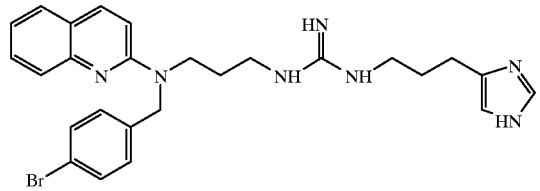

The above benzoyl guanidine (120 mg, 0.19 mmol) was dissolved in 1.5 N hydrochloric acid (3.6 ml) and stirred at 100° C. for 16 h in an ampoule. The cooled reaction mixture was washed with diethyl ether (2×2 ml) and the aqueous phase was evaporated in vacuo. The residue was dissolved in ethanol (10 ml) and evaporated in vacuo. This evaporation procedure was repeated twice. This afforded 116 mg (98%) of the title compound as an amorphous solid.

¹H NMR (200 MHz, MeOD-d₃) d 1.97 (m, 2H), 2.10 (m, 2H), 2.84 (t, 2H), 3.30 (m, 2H), 3.40 (t, 2H), 4.00 (m, 2H), 5.11 (s, 2H), 7.25 (d, 2H), 7.40 (d, 2H), 7.55 (m, 3H), 7.80 (t, 1H), 7.90 (d, 1H), 8.30 (d, 1H), 8.90 (d, 1H), 8.80 (s, 1H).

HPLC retention time=7.15 minutes (5 mM C18 4×250 mm column, eluting with a gradient of 16% acetonitrile/0.1 N aqueous ammonium sulphate to 25% acetonitrile/0.1 N aqueous ammonium sulphate, pH=2.5, over 10 minutes at room temperature).

Example 6

1-(2-(N-(5-Bromopyridin-2-yl)-N-(3,4-dichlorobenzyl)amino)ethyl)-3-(3-(1H-imidazol-4-yl)propyl)thiourea

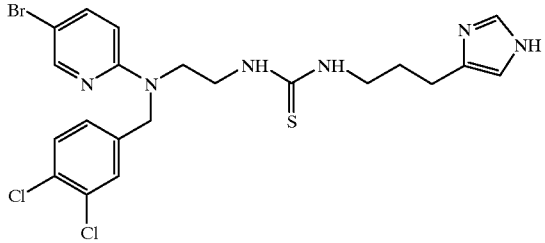

A mixture of 2,5-dibromopyridine (10.0 g, 42.2 mmol) and pyridine (4.24 g, 53.6 mmol) in 1,2-diaminoethane (43 mL) was refluxed under nitrogen for 18 h. The reaction mixture was evaporated under reduced pressure, cooled, and the resulting residue was treated with THF (150 mL) to yield a white precipitate. The precipitate was filtered and washed with additional THF (100 mL). Evaporation of the filtrate afforded a brown oil which was vacuum distilled to give 6.48 g (71%) N-1-(5-bromopyrid-2-yl)ethane-1,2-diamine as a light yellow oil.

bp 134–142° C. (0.6 mm). ¹H NMR (90 MHz CDCl₃)d 1.33 (s, 2H, NH₂), 2.92 (t, 2H), 3.29 (m, 2H), 5.22 (br s, 1H, NH), 6.31 (d, J=9 Hz, 1H, pyridine H-3), 7.44 (dd, J=2.7 Hz, 9 Hz, 1H, pyridine H-4), 8.09 (d, J=2.5 Hz, 1H, pyridine H-6). ¹³C NMR (90 MHz CDCl₃)d 41.22, 44.74, 106.72, 108.67, 139.55, 148.54, 148.70.

A 60% mineral oil dispersion of sodium hydride (0.584 g, 14.6 mmol) and N-1-(5-bromopyrid-2-yl)ethane-1,2- diamine (3.00 g, 13.9 mmol) in DMSO (30 mL) was stirred for 2 h under nitrogen. The suspension was cooled to 0–5° C. and treated dropwise with 3,4-dichlorobenzyl chloride (2.71 g, 13.9 mmol) in DMSO (15 mL). After stirring overnight at room temperature, the reaction mixture was poured into 200 mL of an ice-water mixture. The mixture was extracted with ethyl acetate (3×75 mL), and the combined ethyl acetate extracts were washed with water (2×50 mL), dried ($Na_2SO_4$), filtered, and evaporated to yield an oil. Flash chromatography on silica gel using $CH_2Cl_2$ 90: $CH_3OH$ 5: $Et_3N$ 5 as the solvent system gave 3.5 g (67%) of N-1-(5-bromopyrid-2-yl)-1-(3,4-dichlorobenzyl)ethane-1,2-diamine as a yellow oil.

$^1$H NMR (90 MHz $CDCl_3$)d 1.45 (s, 2H, $NH_2$), 2.92 (t, 2H, $NCH_2$), 3.57 (m, 2H, $CH_2NH_2$), 4.72 (s, 2H, $ArCH_2$), 6.39 (d, J=9 Hz, 1H, pyridine H-3), 7.32 (m, 4H, ArH), 8.16 (d, J=2 Hz, 1H, pyridine H-6). $^{13}$C NMR (90 MHz $CDCl_3$)d 39.82, 51.47, 51.95, 107.00, 107.27, 126.23, 128.77, 130.62, 131.04, 132.73, 138.85, 139.77, 148.66, 156.62.

A mixture of dicyclohexylcarbodiimide (DCC) (2.74 g, 13.2 mmol) and carbon disulfide (10.1 g, 132.6 mmol) in THF (30 mL) was cooled to −10° C. in an ice-salt bath and treated dropwise with a solution of N-1-(5-bromopyrid-2-yl)-1-(3,4-dichlorobenzyl)ethane-1,2-diamine (5.00 g, 13.2 mmol) in THF (20 mL). The reaction mixture was allowed to warm to room temperature and was stirred overnight under nitrogen. Removal of the solvent under reduced pressure afforded a white solid. The solid was triturated with diethyl ether (200 mL), and the dicyclohexylthiourea was removed by filtration. The filtrate was evaporated, and acetonitrile (100 mL) was added to the resulting residue. The remaining dicyclohexyl-thiourea was filtered, and the filtrate was evaporated under vacuum to afford an oil. Flash chromatography on silica gel using $CH_2Cl_2$ 50: hexane 50: $Et_3N$ 1 gave 4.31 g (78%) of 2-[N-(5-bromopyrid-2-yl)-N-(3,4-dichlorobenzyl)]aminoethyl isothiocyanate as a white solid. Recrystallization from diethyl ether/hexane gave an analytical sample.

mp 83–85° C. $^1$H NMR (90 MHz $CDCl_3$)d 3.84 (m, 4H), 4.69 (s, 2H, $ArCH_2$), 6.33 (d, J=8.3 Hz, 1H, pyridine H-3), 7.40 (m, 4H), 8.20 (d, J=2 Hz, 1H, pyridine H-6). $^{13}$C NMR (90 MHz $CDCl_3$)d 43.34, 49.19, 52.71, 107.70, 108.19, 125.74, 128.34, 130.83, 140.10, 148.71, 155.65. Anal. Calcd for $C_{15}H_{12}BrCl_2N_3S$: C, 47.01; H, 3.16; N, 14.62. Found: C, 46.93; H, 3.32; N, 14.56.

A suspension of 3-[1-(triphenylmethyl)imidazol-4-yl]propylamine1 (0.87 g, 2.64 mmol) in THF (40 mL) was stirred under a nitrogen atmosphere at 0–5° C. and treated dropwise with a solution of 2-[N-(5-bromopyrid-2-yl)-N-(3,4-dichlorobenzyl)]aminoethyl isothiocyanate (1.10 g, 2.64 mmol) in THF (15 mL). The reaction mixture was allowed to warm to room temperature and was stirred overnight. TLC on silica gel using EtOAc 90: $CH_3OH$ 5: $Et_3N$ 5 indicated that considerable starting material remained. The reaction mixture was refluxed for 24 h, and the solvent was removed under reduced pressure to yield a white foam. Flash chromatography on silica gel using EtOAc 90: $CH_3OH$ 5: $Et_3N$ 5 as the solvent afforded 1.72 g (87%) of the trityl-protected thiourea as a colorless oil. The oil was suspended in 2 N HCl (40 mL) and was refluxed for 8 h under nitrogen. The precipitated triphenylmethanol was filtered, and the filtrate was evaporated under reduced pressure to yield a foam. The foam was suspended in 1 N NaOH (60 mL) and extracted with EtOAc (3×75 mL). The combined ethyl acetate extracts were washed with water (2×50 mL), dried ($Na_2SO_4$), filtered, and evaporated to yield upon trituration with hexane 765 mg (57%) the title compound as a white hygroscopic foam.

$^1$H NMR (90 MHz $CDCl_3$)d 1.90 (m, 2H), 2.64 (m, 6H), 3.55 (m, 6H), 4.62 (s, 2H, $ArCH_2$), 6.44 (d, J=9 Hz, 1H, pyridine H-3), 7.20–7.55 (m, 8H, NHC=SNH and ArH), 8.09 (d, J=2.5 Hz, 1H, pyridine H-6). $^{13}$C NMR (90 MHz $CDCl_3$)d 23.49, 28.87, 42.42, 43.50, 47.84, 51.79, 107.51, 108.19, 115.99, 126.01, 128.50, 130.78, 131.31, 132.89, 134.35, 137.22, 137.98, 140.26, 148.04, 156.62, 181.75. Anal. Calcd for $C_{21}H_{23}BrCl_2N_6S$: C, 46.50; H, 4.28; N, 15.50. Found: C, 45.13; H, 5.00; N, 16.22.

Example 7

1-(2-(N-(5-Bromopyridin-2-yl)-N-(3,4-dichlorobenzyl)amino)ethyl)-3-(2-(1H-imidazol-4-yl)ethyl)thiourea

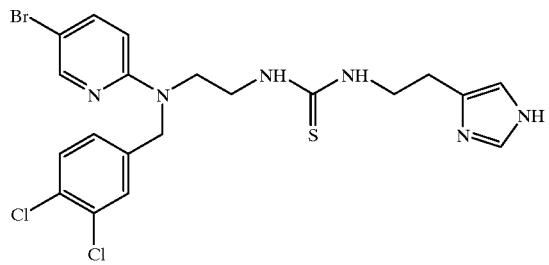

A suspension of histamine (320 mg, 2.88 mmol) in THF (40 mL) was treated with a solution of 2-[N-(5-bromopyrid-2-yl)-N-(3,4-dichlorobenzyl)]aminoethyl isothiocyanate (1.20 g, 2.88 mmol) in THF (15 mL). The reaction mixture was stirred for 48 h under a nitrogen atmosphere, and the solvent was removed under reduced pressure to afford a foam. Flash chromatography on silica gel using a solvent system of EtOAc 90: $CH_3OH$ 5: concentrated $NH_4OH$ 5 gave 987 mg (67%) of the title compound as a white foam.

mp 72–78° C. $^1$H NMR (90 MHz $CDCl_3$)d 2.85 (m, 2H), 3.68 (m, 6H), 4.59 (s, 2H, $ArCH_2$), 6.40 (d, 1H, pyridine H-3), 6.80–7.50 (m, 9H, NHC=SNH and ArH), 8.02 (d, 1H, pyridine H-6). $^{13}$C NMR (90 MHz $CDCl_3$)d 27.66, 42.81, 47.74, 51.80, 107.49, 108.19, 116.16, 125.96, 130.84, 131.33, 132.95,134.90, 135.55, 137.82, 140.32, 148.12, 156.63, 181.71. Anal. Calcd for $C_{20}H_{21}BrCl_2N_6S$: C, 45.46; H, 4.01; N, 15.91. Found: C, 44.90; H, 424; N, 15.79.

Example 8

1-(2-(N-(5-Nitropyridin-2-yl)-N-(3,4-dichlorobenzyl)amino)ethyl)-3-(3-(1H-imidazol-4-yl)propyl)thiourea

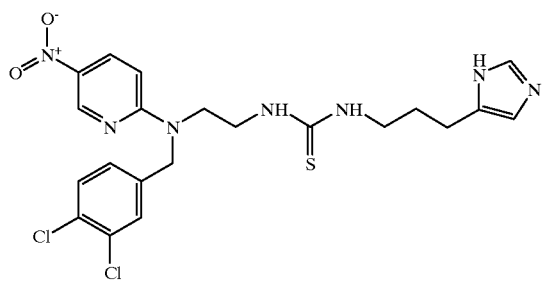

In a similar manner as described for the synthesis of N-1-(5-bromopyrid-2-yl)-1-(3,4-dichlorobenzyl)ethane-1,2-diamine, sodium hydride (0.692 g, 17.3 mmol), N-1-(5-nitropyrid-2-yl)ethane-1,2-diamine (3.00 g, 16.5 mmol), and 3,4-dichlorobenzyl chloride (3.22 g, 16.5 mmol) in DMSO (25 mL) gave an oil. Flash chromatography on silica gel using EtOAc 60: CH₃OH 40: concentrated NH₄OH 1 as the solvent yielded 2.84 g (51%) of N-1-(5-nitropyrid-2-yl)-1-(3,4-dichlorobenzyl)ethane-1,2-diamine as an oil.

$^1$H NMR (90 MHz CDCl$_3$)d 1.35 (br s, 2H, NH$_2$), 3.68 (t, 2H), 4.88 (s, 2H) 6.55 (d, J=9.6 Hz, 1H, pyridine H-3), 7.30 (m, 3H), 8.23 (dd, J=2.7 Hz, 9.3 Hz, 1H, pyridine H-4), 9.08 (d, J=2.9 Hz, 1H, pyridine H-6). $^{13}$C NMR (90 MHz CDCl$_3$)d 39.71, 51.74, 52.12, 104.61, 126.23, 128.83, 130.83, 133.11, 137.33, 146.49.

Using a similar procedure as described for the synthesis of 2-[N-(5-bromopyrid-2-yl)-N-(3,4-dichlorobenzyl)]aminoethyl isothiocyanate, DCC (1.70 g, 8.21 mmol), carbon disulfide (6.70 g, 88 mmol), and N-1-(5-nitropyrid-2-yl)-1-(3,4-dichlorobenzyl) ethane-1,2-diamine (2.80 g, 8.21 mmol) in THF (60 mL) gave a dark yellow solid. Flash chromatography on silica gel using hexane 50: CH$_2$Cl$_2$ 50: Et$_3$N 1 as the solvent system gave 2.20 g (71%) of 2-[N-(3,4-dichlorobenzyl)-N-(5-nitropyrid-2-yl)]aminoethyl isothiocyanate as a yellow solid. mp 104–106° C.

$^1$H NMR d 3.94 (m, 4H), 4.85 (s, 2H, ArCH$_2$), 6.49 (d, J=10 Hz, 1H, pyridine H-3), 7.29 (m, 3H, ArH), 8.23 (dd, J=2.7 Hz, 9.3 Hz, 1H, pyridine H-4), 9.08 (d, J=2 Hz, 1H, pyridine H-6). Anal. Calcd for C$_{15}$H$_{12}$Cl$_2$N$_4$O$_2$S: C, 47.01; H, 3.16; N, 14.62. Found: C, 46.93; H, 3.32; N, 14.56.

A suspension of 3-[1-(triphenylmethyl)imidazol-4-yl]propylamine (959 mg, 2.61 mmol) in THF (20 mL) was cooled to 0–5° C. in an ice-water bath and treated dropwise with 2-[N-(3,4-dichlorobenzyl)-N-(5-nitropyrid-2-yl)]aminoethyl isothiocyanate (1.00 g, 2.61 mmol) in THF (40 mL). After stirring overnight at room temperature under a nitrogen atmosphere, the solvent was removed under reduced pressure to yield 2.1 g of a yellow foam. The intermediate trityl-protected thiourea was suspended in 1 N HCl (35 mL) and refluxed for 1.5 h. The solution was filtered, extracted with diethyl ether (2×200 mL), basified with 6 N NaOH, and extracted with EtOAc (3×100 mL). The combined ethyl acetate extracts were washed with water (3×100 mL), dried (Na2SO4), and evaporated under vacuum to yield a foam. Flash chromatography on silica gel using a solvent system of CH$_2$Cl$_2$ 90: CH$_3$OH 10:concentrated NH$_4$OH 1 yielded 500 mg (38%) of the title compound as a yellow foam.

$^1$H NMR (DMSO-d$_6$) d 1.72 (m, 2H), 3.50 (m, 8H), 4.93 (s, 2H, ArCH$_2$), 6.75 (s, 1H), 7.35 (m, 7H), 8.22 (dd, 1H, pyridine H-4), 8.97 (d, J=2.7 Hz, 1H, pyridine H-6).

$^{13}$C NMR (90 MHz CDCl$_3$)d 23.14, 28.99, 42.05, 42.40, 48.01, 51.58, 105.27, 126.45, 128.89, 130.89, 133.17, 133.98, 146.28, 160.58, 181.46. Anal. Calcd for C$_{21}$H$_{23}$Cl$_2$N$_7$O$_2$S: C, 49.60; H, 4.57; N, 19.29. Found: C, 49.89; H, 4.86; N, 18.86.

Example 9

1-(2-(N-(5-Bromopyridin-2-yl)-N-(3,4-dichlorobenzyl)amino)ethyl)-3-(3-(pyrrolidin-1-yl)propyl)thiourea

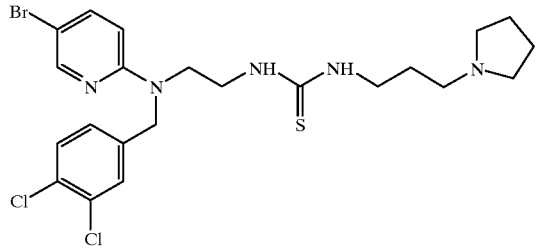

A solution of N-(3-aminopropyl)pyrrolidine (354 mg, 2.76 mmol) in THF (50 mL) was cooled to 0–5° C. in an ice-water bath under a nitrogen atmosphere and treated with 2-[N-(3,4-dichlorobenzyl)-N-(5-nitropyrid-2-yl)]aminoethyl isothiocyanate (1.19 g, 2.76 mmol) in THF (25 mL). The reaction mixture was allowed to warm to room temperature and was stirred overnight. Removal of the solvent under reduced pressure afforded an oil which solidified upon trituration with hexane-EtOAc. Recrystallization from EtOAc-hexane afforded 1.03 g (66%) of the title compound as a white solid.

mp 123–125° C. $^1$H NMR (90 MHz CDCl$_3$)d 1.77 (m, 6H), 2.45 (m, 6H), 3.50 (m, 6H), 4.68 (s, 2H, ArH), 6.50 (d, 1H), 7.00–7.55 (m, 6H), 8.16 (d, J=2.2 Hz, 1H). $^{13}$C NMR (90 MHz CDCl$_3$)d 23.62, 28.17, 43.07, 47.89, 51.74, 107.59, 108.08, 126.33, 128.83, 130.94,138.47, 140.26, 148.55, 156.84, 183.0. Anal. Calcd for C$_{22}$H$_{28}$BrCl$_2$N$_5$S: C, 48.44; H, 5.18; N, 12.84. Found: C, 48.40; H, 5.26; N, 12.77.

Example 10

1-(2-(N-(5-Bromopyridin-2-yl)-N-(3,4-dichlorobenzyl)amino)ethyl)-3-(3-dimethylaminopropyl)thiourea

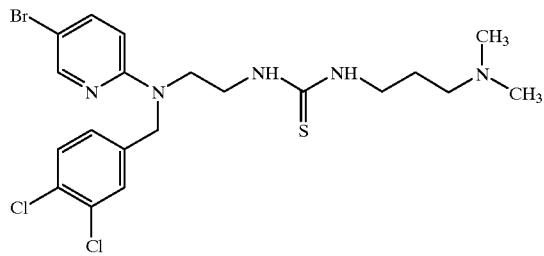

A solution of N-1-(5-bromopyrid-2-yl)-1-(3,4-dichlorobenzyl)ethane-1,2-diamine (1.00 g, 2.67 mmol) in THF (25 mL) was cooled to 0–5° C. under a nitrogen atmosphere and treated dropwise with a solution of 3-(dimethylamino)propyl isothiocyanate (385 mg, 2.67 mmol) in THF (15 mL). After stirring overnight at room temperature, the solvent was removed under reduced pressure to afford an oil. Flash chromatography on silica gel using a solvent system of EtOAc 85: CH$_3$OH 15: concentrated NH$_4$OH 1 gave 900 mg (65%) of the title compound as a white foam.

$^1$H NMR (90 MHz CDCl$_3$)d 1.70 (9 m, 2H), 1.95–2.45 (m, including a singlet at 2.23 N(CH$_3$)$_2$, 8H), 2.50–3.95 (m, 6H), 4.68 (s, 2H, ArCH$_2$), 6.47 (d, J=9 Hz, 1H), 7.20 (m, 6H), 7.55 (d, J=2.2 Hz, 1H), 8.18 (d, J=2.5 Hz, 1H). $^{13}$C NMR (90 MHz CDCl$_3$)d 26.32, 43.11, 44.85, 47.67, 51.52, 57.28, 107.97, 126.06, 128.55, 130.77, 131.26, 132.89, 138.09, 140.15, 148.33, 156.72, 182.46.

Example 11

1-(3-(N-(4-Bromobenzyl)-N-(pyridin-2-yl)amino) propyl)-3-(3-(imidazol-1-yl)propyl)thiourea dihydrobromide

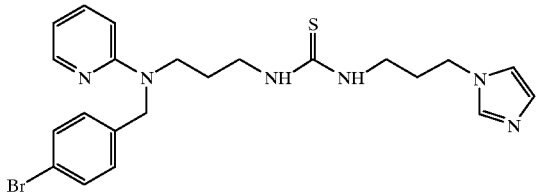

Following the method for the synthesis of N-1-(5-bromopyrid-2-yl)ethane-1,2-diamine, 2-bromopyridine (20.0 g, 126.7 mmol), pyridine (12.7 g, 160.8 mmol), and 1,3-diaminopropane (47.4 g, 639 mmol) afforded a dark brown oil. Vacuum distillation gave 9.19 g (48%) of a N-1-(pyrid-yl)propane-1,3-diamine as a light yellow oil.

bp 111–114° C. (0.65 mm). $^1$H NMR (90 MHz CDCl$_3$)d 1.28 (br s, 2H, NH2) 1.75 (m, 2H), 2.84 (t, 2H), 3.35 (m, 2H), 5.00 (br s, 2H, NH), 6.50 (m, 2H), 7.40 (ddd, 1H), 8.07 (m, 1H). $^{13}$C NMR (90 MHz CDCl$_3$)d 32.93, 39.92 (2X), 106.77, 112.30, 137.17, 148.00, 159.00.

Following the procedure described for the synthesis of N-1-(5-bromopyrid-2-yl)-1-(3,4-dichlorobenzyl)ethane-1,2-diamine, N-1-(pyrid-yl)propane-1,3-diamine (5.00 g, 33.1 mmol), sodium hydride as a 60% mineral oil dispersion (1.39 g, 34.8 mmol), and 4-bromobenzyl bromide (8.27 g, 33.1 mmol) in DMSO (50 mL) gave a yellow oil. Flash chromatography on silica gel using CH$_2$Cl$_2$ 90: CH$_3$OH 5: Et$_3$N 5 as the solvent system afforded 2.28 g (22%) of N-1-(4-bromobenzyl)-1-(pyrid-2-yl)propane-1,3-diamine as a light yellow oil.

$^1$H NMR (90 MHz CDCl$_3$)d 1.75 (m, 4H, CH$_2$ and NH$_2$), 2.72 (t, 2H), 3.59 (t, 2H, NCH$_2$), 4.72 (s, 2H, ArCH$_2$), 6.38–7.00 (m, 7H, ArH), 8.16 (d, 1H, pyridine H-6). $^{13}$C NMR (90 MHz CDCl$_3$)d 31.21, 39.50, 45.73, 50.98, 105.81, 112.04, 120.60, 128.62, 131.65, 137.34, 137.93, 148.07, 158.20.

A solution of N-1-(4-bromobenzyl)-1-(pyrid-2-yl) propane-1,3-diamine (616 mg, 1.92 mmol) in THF (15 mL) was treated dropwise with 3-(imidazol-1-yl)propyl isothiocyanate (323 mg, 1.92 mmol) in THF (10 mL) under a nitrogen atmosphere. After stirring overnight at room temperature, the solid was filtered. Evaporation of the filtrate under reduced pressure gave a yellow oil which was dissolved in methanol and acidified with methanolic hydrogen bromide. Addition of diethyl ether afforded a cloudy solution which produced a light tan solid upon standing in the refrigerator. The solid was filtered and dried to yield 0.94 g (75%) of the title compound. Recrystallization from absolute ethanol-diethyl ether afforded an analytical sample.

mp 199–201° C. $^1$H NMR (DMSO-d$_6$) d 1.55–2.25 (m, 4H, CH2), 3.20–3.90 (m, 6H, CH$_2$), 4.26 (t, 2H, CH$_2$-imidazole), 7.00 (t, 1H), 7.26 (d, J=8.3 Hz, 2H, 2,6H of C$_6$H$_4$-4-Br), 7.57 (d, J=8.3 Hz, 3,5H of C$_6$H$_4$-4-Br), 7.86 (m, 9H). $^{13}$C NMR (DMSO-d6) d 25.57, 29.09, 37.87, 39.98, 46.10, 47.40, 51.57, 111.76, 112.20, 121.78, 131.37, 134.73, 135.11, 137.44, 143.40, 151.27, 181.66. Anal. Calcd for C$_{22}$H$_{29}$Br$_3$N$_6$S: C, 40.69; H, 4.51; N, 12.95. Found: C, 39.96; H, 4.52; N, 12.65.

Example 12

1-(3-(N-(4-Bromobenzyl)-N-(pyridin-2-yl)amino) propyl)-3-(4-(N-(pyridin-2-yl)amino)propyl)thiourea

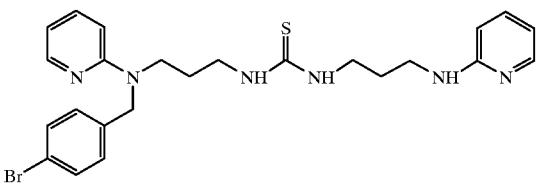

Following the method for the synthesis of N-1-(5-bromopyrid-2-yl)ethane-1,2-diamine, 2-bromopyridine (20.0 g, 126.7 mmol), pyridine (12.7 g, 160.8 mmol), and 1,3-diaminopropane (47.4 g, 639 mmol) afforded a dark brown oil. Vacuum distillation gave 9.19 g (48%) of a N-1-(pyrid-yl)propane-1,3-diamine as a light yellow oil.

bp 111–114° C. (0.65 mm). $^1$H NMR (90 MHz CDCl$_3$)d 1.28 (br s, 2H, NH$_2$), 1.75 (m, 2H), 2.84 (t, 2H), 3.35 (m, 2H), 5.00 (br s, 2H, NH), 6.50 (m, 2H), 7.40 (ddd, 1H), 8.07 (m, 1H). $^{13}$C NMR (90 MHz CDCl$_3$)d 32.93, 39.92 (2X), 106.77, 112.30, 137.17, 148.00, 159.00.

A solution of N-1-(pyridyl)propane-1,3-diamine (419 mg, 2.76 mmol) in THF (25 mL) was cooled to 0–5 ° C. under a nitrogen atmosphere and treated dropwise with 3-[N-(4-bromobenzyl)-N-(pyrid-2-yl)]aminopropyl isothiocyanate (1.00 g, 2.76 mmol) in THF (10 mL). After stirring overnight at room temperature, the solvent was removed under reduced pressure to afford an oil. The oil was flash chromatographed on silica gel using a solvent system of CH$_2$Cl$_2$ 90: CH$_3$OH 5: Et$_3$N 5 to yield 9, 50 mL fractions. Fractions 3–9 were combined and the solvents were removed under reduced pressure to give 1.31 g (92%) of the title compound as an oil (R$_f$=0.5).

$^1$H NMR (90 MHz CDCl$_3$)d 1.82–2.40 m, 7H), 3.58 (m, 5H), 4.57 (s, 2H, ArCH$_2$), 4.75 (br m, NH), 6.35–8.14 (m, 14H). $^{13}$C NMR (90 MHz CDCl$_3$)d 27.14, 29.53, 38.63, 41.17, 45.34, 51.30, 106.40, 108.29, 112.52, 112.85, 120.86, 128.18, 131.81, 136.68, 137.39, 137.77, 147.63, 158.73, 181.05. MS (Cl, CH$_4$)m/z 513 (M$^+$). Anal. Calcd for C$_{24}$H$_{29}$BrN$_6$S: C, 56.14; H, 5.69; N, 16.37. Found: C, 56.10; H, 5.73; N, 16.34.

Example 13

1-(3-(N-(5-Bromopyridin-2-yl)-N-(3,4-dichlorobenzyl)amino)propyl)-3-(3-(imidazol-1-yl)propyl)thiourea

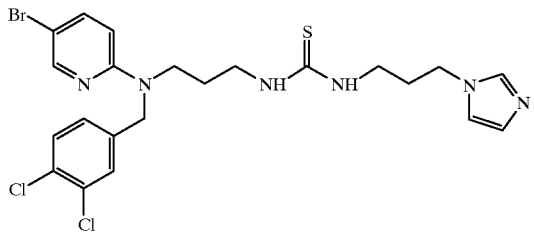

Following the method described for the synthesis of N-1-(5-bromopyrid-2-yl)-1-(3,4-dichlorobenzyl)ethane-1,2-diamine, N-1-(5-bromopyrid-yl)propane-1,3-diamine (5.00 g, 21.7 mmol), a 60% mineral oil suspension of of sodium hydride (0.914 g, 22.9 mmol), and 3,4-dichlorobenzyl chloride (4.25 g, 21.7 mmol) in DMSO (45 mL) gave an oil. Flash chromatography on silica gel using $CH_2Cl_2$ 90: $CH_3OH$ 5:$Et_3N$ 5 as the solvent yielded 4.92 g (58%) of the N-1-(5-bromopyrid-2-yl)-1-(3,4-dichlorobenzyl)propane-1,3-diamine as an oil.

$^1$H NMR (90 MHz $CDCl_3$)d 1.44 (s, 2H, $NH_2$), 1.80 (m, 2H), 2.73 (t, 2H), 3.56 (t, 2H), 4.66 (s, 2H, $ArCH_2$), 6.37 (d, J=9 Hz, 1H, pyridine H-3), 7.31 (m, 4H), 8.15 (d, J=2.5 Hz, 1H, pyridine H-6). $^{13}$C NMR (90 MHz $CDCl_3$)d 30.93, 39.44, 46.21, 50.71, 106.67, 107.16, 126.23, 128.72, 130.51, 130.89, 132.62, 138.90, 139.66, 148.55, 156.46.

A solution of N-1-(5-bromopyrid-2-yl)-1-(3,4-dichlorobenzyl)propane-1,3-diamine (1.00 g, 2.57 mmol) in THF was cooled to 0–5° C. under a nitrogen atmosphere and treated dropwise with 3-(1-imidazolyl)propyl isothiocyanate (432 mg, 2.57 mmol) in THF (15 mL). The reaction mixture was allowed to warm to room temperature and was stirred overnight. Removal of the solvent under reduced pressure afforded a semisolid. Trituration with diethyl ether-petroleum ether gave a solid which was recrystallized from ethyl acetate-diethyl ether to yield 450 mg (31%) of the title compound.

mp 94–97° C. (decomposition). $^1$H NMR (90 MHz $CDCl_3$)d 1.60–2.35 (m, 4H), 3.54 (m, 5H), 4.05 (t, 2H, $CH_2$-imidazole) 4.57 (s, 2H, $ArCH_2$), 6.28 (d, J=9 Hz, 1H), 6.99 (d, J=4.4 Hz, 1H), 7.19 (m, 9H). $^{13}$C NMR (90 MHz $CDCl_3$)d 27.03, 30.91, 41.01, 41.50, 44.59, 45.94, 51.03, 107.05, 107.64, 119.18, 125.90, 128.39, 129.21, 130.78, 131.21, 132.89, 136.95, 137.98, 140.04, 148.33, 156.62, 182.62. Anal. Calcd for $C_{22}H_{25}BrCl_2N_6S$: C, 47.49; H, 4.53; N, 15.11. Found: C, 47.23; H, 4.59; N, 14.98.

Example 14

1-(3-(N-(5-Bromopyridin-2-yl)-N-(3,4-dichlorobenzyl)amino)propyl)-3-(4-(N-(pyridin-2-yl)amino)propyl)thiourea

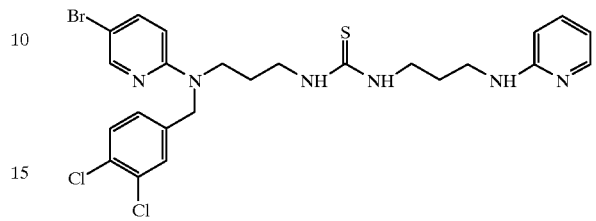

Using the general method, DCC (1.94 g, 9.35 mmol), carbon disulfide (7.62 g, 100 mmol), and N-1-(5-bromopyrid-2-yl)-1-(3,4-dichlorobenzyl)propane-1,3-diamine (3.64 g, 9.35 mmol) in THF (45 mL) gave an oil. Purification by flash chromatography on silica gel using hexane 70: EtOAc 30:$Et_3N$ 1 as the solvent afforded 3.19 g (79%) of 3-[N-(5-bromopyrid-2-yl)-N-(3,4-dichlorobenzyl)]aminopropyl isothiocyanate as an oil.

$^1$H NMR (90 MHz $CDCl_3$)d 2.06 (m, 2H), 3.62 (m, 4H), 4.66 (s, 2H, $ArCH_2$), 6.40 (m, 1H), 7.35 (m, 4H), 8.22 (m, 1H). $^{13}$C NMR d 28.06, 42.91, 46.10, 51.41, 107.21, 107.43, 126.17, 128.72, 130.72, 131.26, 138.31, 139.93, 148.76, 156.13. MS (CI, $CH_4$) 432 M$^+$. Anal. Calcd for $C^{15}H_{14}BrCl_2N_3S$: C, 44.56; H, 3.28; N, 9.75. Found: C, 44.39; H, 3.42; N, 9.79.

A solution of N-1-(4-bromobenzyl)-1-(pyrid-2-yl)propane-1,3-diamine (352 mg, 2.32 mmol) in THF (30 mL) was cooled to 0–5° C. under nitrogen and treated dropwise with of 3-[N-(5-bromopyrid-2-yl)-N-(3,4-dichlorobenzyl)]aminopropyl isothiocyanate (1.00 g, 2.32 mmol) in THF (20 mL). After stirring at room temperature overnight, the solvent was removed under reduced pressure to afford an oil. Flash chromatography on silica gel using a solvent system of $CH_2Cl_2$ 98: $CH_3OH$ 1: $Et_3N$ 1 gave the title compound as an oil which solidified upon trituration with hexane. Recrystallization from ethyl acetate-hexane gave a hygroscopic solid.

mp 88° C. (decomposition); $^1$H NMR (90 MHz $CDCl_3$)d 0.90–2.10 (m, 4H), 3.50 (m, 8H), 4.57 (s, 2H, $ArCH_2$), 4.90 (br s, 1H, NH), 6.30 (d, J=9.3 Hz, 1H, pyridine H-3), 6.45–8.18 (m, 11H, ArH and NHC=SNH); $^{13}$C NMR (90 MHz $CDCl_3$)d 27.09, 29.64, 38.63, 41.34, 41.45, 46.05, 51.14, 107.16, 107.65, 108.57, 112.90, 125.99, 128.51, 130.78, 131.21, 132.89, 137.55, 138.15, 140.10, 147.30, 148.50, 156.62, 158.79, 181.43; MS (CI, $CH_4$) m/z 583 (M$^+$). Anal. Calcd for $C_{24}H_{27}BrCl_2N_6S$: C, 49.50; H, 4.67; N, 14.43. Found: C, 49.28; H, 4.57; N, 14.21.

Example 15

1-(3-(N-(5-Bromopyridin-2-yl)-N-(3,4-dichlorobenzyl)amino)propyl)-3-(3-(1H-imidazol-4-yl)propyl)thiourea

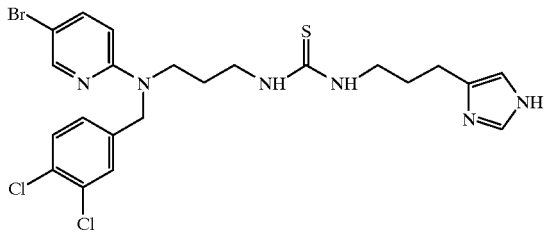

A suspension of 3-[1-(triphenylmethyl)imidazol-4-yl]propylamine (1.32 g, 3.60 mmol) in THF (50 mL) was treated dropwise with of 3-[N-(5-bromopyrid-2-yl)-N-(3,4-dichlorobenzyl)]aminopropyl isothiocyanate (1.55 g, 3.60 mmol) in THF (25 mL) at 0–5° C. under a nitrogen atmosphere. The reaction mixture was allowed to warm to room temperature and was stirred overnight. Removal of the solvent under reduced pressure afforded an oil. Flash chromatography on silica gel using a solvent system of EtOAc 92: CH$_3$OH 4: Et$_3$N 4 gave 2.10 g (73%) of the trityl-protected thiourea. The oil was suspended in 2 N HCl (50 mL) and was refluxed for 7 h. The precipitated triphenyl-methanol was filtered, and the aqueous acid was evaporated under reduced pressure to yield a foam. The hygroscopic hydrochloride was converted to the free base with 1 N NaOH, and the aqueous layer was extracted with EtOAc (3×75 mL). The combined extracts were washed with water (2×50 mL), dried (Na$_2$SO$_4$), filtered, and evaporated to afford 600 mg of a foam. Purification by flash chromatography on silica gel using EtOAc 85: CH$_3$OH 15: concentrated NH$_4$OH 1 as the solvent system gave 533 mg (27%) of the title compound as a solid foam.

$^1$H NMR (90 MHz CDCl$_3$)d 2.05 (m, 4H), 2.70 (m, 2H), 3.59 (m, 6H), 4.59 (s, ArCH$_2$), 6.30 (d, J=9.3 Hz, 1H), 6.50–8.11 (m, 9H); $^{13}$C NMR (90 MHz CDCl$_3$)d 23.73, 27.03, 28.82, 41.88, 43.29, 46.10, 106.99, 107.70, 115.93, 126.01, 128.50, 130.72, 131.10, 132.78, 134.41, 137.39, 138.20, 140.04, 148.33, 156.56, 181.38. Anal. Calcd. for C$_{22}$H$_{25}$BrCl$_2$N$_6$S: C, 47.49; H, 4.54; N, 15.11. Found: C, 47.48; H, 4.48; N, 14.96.

Example 16

1-(3-(N-(5-Bromopyridin-2-yl)-N-((naphth-1-yl)methyl)amino)propyl)-3-(3-(1H-imidazol-4-yl)propyl)thiourea

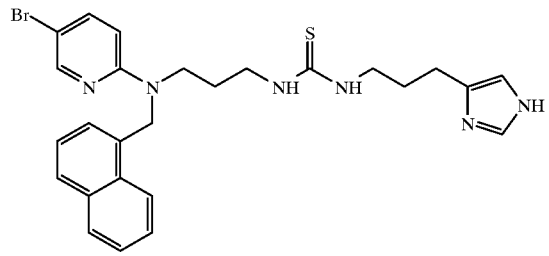

According to the method for the synthesis of N-1-(5-bromopyrid-2-yl)ethane-1,2-diamine, 2,5-dibromopyridine (4.40 g, 18.6 mmol), pyridine (1.86 g, 23.6 mmol), and 1,3-diaminopropane (25 mL) yielded an oil. Vacuum distillation afforded 2.69 g (63%) of N-1-(5-bromopyrid-yl)propane-1,3-diamine as an oil.

bp 135–139° C. (0.1 mm); $^1$H NMR (90 MHz CDCl$_3$)d 1.52 (br s, 2H, NH$_2$), 1.72 (m, 2H), 2.89 (t, 2H), 3.36 (m, 2H), 5.30 (br s, 1H, NH), 6.29 (d, J=9 Hz, 1H, pyridine H-3), 7.44 (dd, J=2.4 Hz, J=8.8 Hz, 1H, pyridine H-4), 8.09 (d, J=2.4 Hz, 1H, pyridine H-6); $^{13}$C NMR (90 MHz CDCl$_3$)d 32.61, 39.98, 40.25, 106.45, 108.29, 139.50, 148.49, 157.48.

N-[1-(5-bromopyrid-2-yl)-1-(naphthal-1-yl)methyl]propane-1,3-diamine (3e). Using the method described for the synthesis of N-1-(5-bromopyrid-2-yl)-1-(3,4-dichlorobenzyl)ethane-1,2-diamine, N-1-(5-bromopyrid-yl)propane-1,3-diamine (8.71 g, 37.9 mmol), a 60% mineral oil dispersion of sodium hydride (1.67 g, 41.6 mmol), and 1-(bromomethyl)naphthalene (9.21 g, 41.6 mmol) in DMSO (60 mL) gave an oil. Flash chromatography on silica gel using CH$_2$Cl$_2$ 50: CH$_3$OH 50: concentrated ammonium hydroxide 1 afforded 5.10 g (35%) of N-[1-(5-bromopyrid-2-yl)-1-(naphthal-1-yl)methyl]propane-1,3-diamine as an oil.

$^1$H NMR (90 MHz CDCl$_3$)d 1.43 (br s, 2H, NH$_2$), 1.75 (m, 2H), 3.67 (t, 2H), 5.12 (s, 2H, CH$_2$-a-naphthalylmethyl) 6.31 (d, J=9 Hz, 1H, pyridine H-3), 7.15–8.05 (m, 8H, ArH), 8.20 (d, J=2.4 Hz, 1H, pyridine H-6); $^{13}$C NMR (90 MHz CDCl$_3$)d 31.31, 39.55, 45.72, 49.62, 106.29, 107.54, 122.76, 123.84, 125.47, 125.85, 126.23, 127.74, 128.94, 131.32, 132.24, 133.92, 139.55, 148.55, 156.94.

Following the procedure described for the preparation of 2-[N-(5-bromopyrid-2-yl)-N-(3,4-dichlorobenzyl)]aminoethyl isothiocyanate, DCC (2.32 g, 10.8 mmol), carbon disulfide (8.80 g, 115 mmol) and N-[1-(5-bromopyrid-2-yl)-1-(naphthal-1-yl)methyl]propane-1,3-diamine (4.00 g, 10.8 mmol) in THF (140 mL) afforded an oil. Flash chromatography on silica gel using a solvent system of hexane 50: CH$_2$Cl$_2$ 50: Et$_3$N 1 gave 2.70 g (84%) of 3-[N-(5-bromopyrid-2-yl)-N-(naphthal-1-yl)methyl]aminopropyl isothiocyanate as a colorless oil.

$^1$H NMR (90 MHz CDCl$_3$)d 2.00 (m, 2H, NCH$_2$CH$_2$CH$_2$N=C), 3.54 (t, 2H), 3.74 (t, 2H), 5.11 (s, 2H, ArCH$_2$), 6.30 (d, J=9 Hz, 1H, pyridine H-3), 7.15–8.02 (m, 8H, ArH), 8.25 (d, J=2.4 Hz, 1H, pyridine H-6); $^{13}$C NMR d 28.28, 43.01, 45.77, 50.32, 106.99, 107.59, 122.65, 123.89, 125.41, 125.90, 126.39, 127.96, 128.93, 139.71, 148.60, 156.62.

A solution of 3-[1-(triphenylmethyl)imidazol-4-yl]propylamine (1.24 g, 3.38 mmol) was dissolved in THF (20 mL) and treated dropwise with a solution of 3-[N-(5-bromopyrid-2-yl)-N-(naphthal-1-yl)methyl]aminopropyl isothiocyanate (1.40 g, 3.38 mmol) in THF (20 mL) at 0–5° C. under a nitrogen atmosphere. The reaction mixture was allowed to warm to room temperature and was stirred overnight. The solvent was evaporated under reduced pressure to yield an oil which was purified by flash chromatography on silica gel using a solvent system of EtOAc 92: CH$_3$OH 4: Et$_3$N 4. Fractions homogeneous on TLC were combined and evaporated to give 2.63 g of the trityl-protected thiourea. The oil was suspended in 1 N HCl (60 mL) and refluxed for 1.5 h. The precipitate was filtered, and the filtrate was extracted with diethyl ether (2×100 mL). The aqueous layer was basified with 6 N NaOH and extracted with ethyl acetate (3×100 mL). The combined ethyl acetate extracts were washed with water (2×50 mL), dried (Na$_2$SO$_4$), filtered, and evaporated to yield an oil. Flash chromatography on silica gel using an eluent of CH$_2$Cl$_2$ 90:

CH₃OH 10: concentrated NH₄OH 1 afforded 1.10 g (61%) of the title compound as a foam.

¹H NMR (90 MHz CDCl₃)d 1.88 (m, 4H), 2.65 (m, 2H), 3.30–3.80 (m, 6H), 5.02 (s, 2H, 1-naphthalyl-CH₂), 6.18–8.11 (m, 14H, ArH and NHC=SNH); ¹³C (90 MHz CDCl₃)d 24.06, 27.19, 29.38, 42.20, 43.75, 50.94, 108.44, 115.63, 122.50, 123.44, 125.31, 125.94, 126.56, 128.13, 129.38, 131.56, 134.75, 135.00, 138.75, 140.63, 148.44, 157.81, 181.56. Anal. Calcd for C₂₆H₂₉BrN₆S: C, 58.09; H, 5.45; N, 15.64. Found: C, 57.72; H, 5.62; N, 15.61.

Example 17

1-(4-Aminobutyl)-3-(3-(N-(5-bromopyridin-2-yl)-N-((naphth-1-yl)methyl)amino)propyl)thiourea

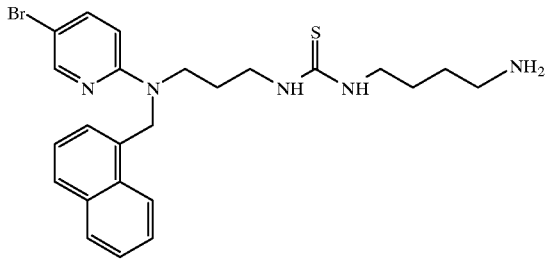

A solution of (4-phthalimido butyl)amine hydrochloride (688 mg, 2.7 mmol) and triethylamine (547 mg, 5.4 mmol) in THF (25 mL) was stirred for 2 h at room temperature. The reaction mixture was treated dropwise with a solution of 3-[N-(5-bromopyrid-2-yl)-N-(naphthal-1-yl)methyl] aminopropyl isothiocyanate (1114 mg, 2.7 mmol) in THF (20 mL), and the mixture was stirred overnight under nitrogen. The precipitated triethylamine hydrochloride was filtered, and the filtrate was evaporated under reduced pressure to afford an oil. Purification by flash chromatography on silica gel using a solvent system of CH₂Cl₂ 100: CH₃OH 2: concentrated NH₄OH 1 gave 1.08 g of a yellow foam. The foam was suspended in a mixture of ethanol (20 mL) and 85% hydrazine hydrate (641 mg, 12.7 mmol), and the mixture was refluxed for 5 h. The mixture was filtered to remove the precipitated phthalhydrazide, and the solvent was removed under reduced pressure to yield an oily residue. The oil was dissolved in CH₂Cl₂ (75 mL), washed with water (3×50 mL), separated, dried (Na₂SO₄), filtered, and evaporated to yield 700 mg of the amine as a light yellow foam. Flash chromatography on silica gel using EtOAc 50: CH₃OH 50: concentrated NH₄OH 1 as the solvent yielded 650 (48%) of the title compound as a white foam.

¹H NMR (90 MHz CDCl₃)d 1.70 (m, 10H), 2.79 (m, 2H), 3.70 (m, 6H), 5.06 (s, 2H, ArCH₂), 6.29 (d, 9 Hz, 1H), 6.70–8.20 (m, 11H); ¹³C NMR (90 MHz CDCl₃)d 26.32, 27.18, 30.27, 41.43, 41.59, 43.71, 45,39, 49.83, 106.66, 108.34, 122.37, 123.07, 125.45, 126.00, 126.43, 127.95, 129.03, 130.82, 131.03, 133.86, 140.08, 147.99, 157.47, 181.03.

Example 18

1-(4-Aminobutyl)-3-[3-[N-(5-bromopyrid-2-yl)]-[N-(3,4-dichlorobenzyl)]aminopropyl]thiourea

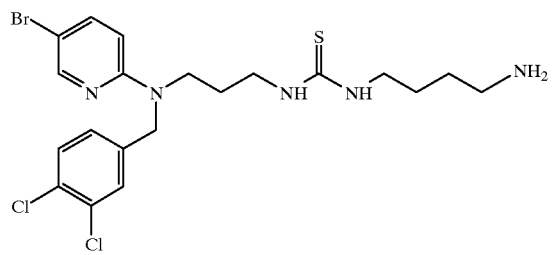

A suspension of (4-phthalimidobutyl)amine hydrochloride (1.50 g, 5.89 mmol) and triethylamine (1.49 g, 14.7 mmol) was stirred under nitrogen for 3 h at room temperature, and a solution of 3-[N-(5-bromopyrid-2-yl)-N-(3,4-dichlorobenzyl)]aminopropyl isothiocyanate (2.54 g, 5.89 mmol) in THF (50 mL) was added dropwise. After stirring overnight, the precipitate was filtered and the filtrate was evaporated under reduced pressure to yield an oil. Flash chromatography on silica gel using CH₂Cl₂ 100: CH₃OH 1:concentrated ammonium hydroxide 1.5 as the solvent afforded 2.06 g of the intermediate phthalimide as an oil. The oil was dissolved in a mixture of 85% hydrazine hydrate (635 mg, 12.7 mmol) and absolute ethanol (75 mL) and refluxed for 8 h. The reaction mixture was cooled, filtered, and evaporated to yield an oil. Absolute ethanol (25 mL) was added and the solution was concentrated under reduced pressure. The resulting residue was partitioned between diethyl ether (200 mL) and water (50 mL), and the diethyl ether phase was separated, dried (Na₂SO₄), filtered, and evaporated under reduced pressure. Flash chromatography on silica gel using EtOAc 50: CH₃OH 50: concentrated NH₄OH 1.2 afforded 1.15 g (70%) the title compound as a colorless oil.

¹H NMR (90 MHz CDCl₃)d 1.66 (m, 6H, CH₂ and NH₂), 2.80 (t, 2H), 3.59 (m, 6H), 4.62 (s, 2H, ArCH₂), 6.35 (d, J=9 Hz, 1H, pyridine H-3), 6.99–7.56 (m, 6H, ArH and NHC=SNH), 8.18 (d, J=2.4 Hz, 1H, pyridine H-6) ¹³C NMR d 26.33, 27.09, 30.28, 41.44, 41.61, 43.83, 50.98, 107.75, 125.90, 128.39, 130.78, 137.87, 140.15, 148.28, 156.78, 181.11. Anal. Calcd. for C₂₀H₂₆BrCl₂N₅S: C, 42.26; H, 5.05; N, 13.49. Found: C, 46.09; H, 5.10; N, 12.90.

Example 19

1-(3-(N-(5-Bromopyridin-2-yl)-N-(3,4-dichlorobenzyl)amino)propyl)-3-(3-(pyrrolidin-1-yl)propyl)thiourea

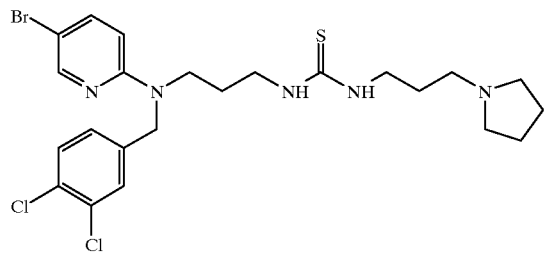

A solution of N-(3-aminopropyl)pyrrolidine (354 mg, 2.76 mmol) in THF (50 mL) was cooled to 0–5° C. under a nitrogen atmosphere and treated dropwise with a solution of 3-[N-(5-bromopyrid-2-yl)-N-(3,4-dichlorobenzyl)] aminopropyl isothiocyanate (1.19 g, 2.76 mmol) in THF (25 mL). The reaction mixture was allowed to warm to room temperature and was stirred overnight. The solvent was removed under reduced pressure to afford an oil which solidified upon trituration with hexane-ethyl acetate. Recrystallization form ethyl acetate-hexane gave 1.03 g (66%) of the title compound as a white solid.

mp 122–124° C.; $^1$H NMR (90 MHz CDCl$_3$)d 1.73 (m, 8H), 2.57 (m, 6H), 3.60 (m, 6H), 4.63 (s, 2H, ArCH$_2$), 6.33 (d, J=9 Hz, 1H, pyridine H-3), 7.00–7.53 (m, 6H, ArH and NHC=SNH), 8.18 (d, J=2.4 Hz, 1H, pyridine H-6); $^{13}$C NMR (90 MHz CDCl$_3$)d 23.46, 27.14, 41.99, 46.16, 51.09, 53.36, 53.69, 107.05, 107.48, 126.12, 128.61, 130.72, 132.72, 132.84, 138.31, 139.99, 148.55, 156.51, 182.13. Anal. Calcd. for C$_{23}$H$_{30}$BrCl$_2$N$_5$S: C, 49.39; H, 5.41; N, 12.52. Found: C, 49.14; H, 5.44; N, 12.45

Example 20

1-(3-(N-(5-Bromopyridin-2-yl)-N-(3,4-dichlorobenzyl)amino)propyl)-3-(2-(pyrid-2-yl)ethyl)thiourea

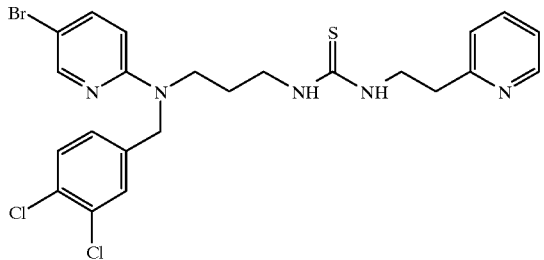

A solution of 2-(2-aminoethyl)pyridine (0.33 g, 2.71 mmol) in THF (50 mL) was cooled to 0–5° C. under a nitrogen atomosphere and treated with a solution of 3-[N-(5-bromopyrid-2-yl)-N-(3,4-dichlorobenzyl)]aminopropyl isothiocyanate (1.17 g, 2.71 mmol) in THF (25 mL). The reaction mixture was allowed to warm to room temperature and was stirred overnight. Removal of the solvent under reduced pressure afforded an oil which was purified by flash chromatography on silica gel using EtOAc 96: CH$_3$OH 4: concentrated NH$_4$OH 1 as the solvent system. Fractions homogeneous by TLC were combined and evaporated to yield 1.11 g (74%) of the title compound as a foam.

$^1$H NMR (90 MHz CDCl$_3$)d 1.78 (m, 2H), 3.00 (t, 2H), 3.69 (m, 6H), 4.59 (s, 2H, ArH), 6.30 (d, J=9 Hz, 1H, pyridine H-3), 6.88–8.49 (m, 11H, ArH and NHC=SNH); $^{13}$C NMR (90 MHz CDCl$_3$) d 26.82, 36.30, 41.34, 43.34, 45.89, 50.93, 107.05, 107.59, 121.84, 123.63, 125.91, 128.40, 130.67, 131.11, 132.79, 136.96, 137.99, 139.99, 148.50, 148.93, 156.57, 159.06, 181.11. Anal. Calcd. for C$_{23}$H$_{24}$BrCl$_2$N$_5$S: C, 49.93; H, 4.37; N, 12.66. Found: C, 49.81; H, 4.43; N, 12.42.

Example 21

1-(4-(N- (4-Bromobenzyl)-N-(pyridin-2-yl)amino) butyl)-3-(3-(imidazol-1-yl)propyl)thiourea

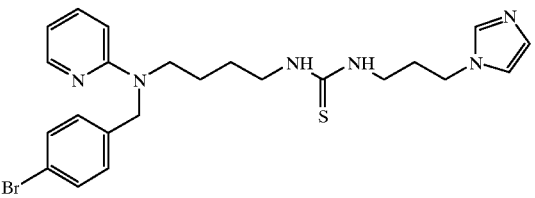

Following the general method described for N-1-(5-bromopyrid-2-yl)ethane-1,2-diamine, 2-bromopyridine (20.0 g, 126.7 mmol), 1,4-diaminobutane (56.3 g, 639 mmol), and pyridine (12.7 g, 160.8 mmol) gave 11.5 g (55%) of N-1-(pyrid-2-yl)butane-1,4-diamine as a light yellow oil.

bp 103–105° C. (0.05 mm); $^1$H NMR (90 MHz CDCl$_3$)d 1.56 (br s, 2H, NH$_2$), 1.61 (m, 4H), 2.73 (t, 2H), 3.25 (m, 2H), 4.73 (br s, 1H, NH), 6.43 (m, 2H), 7.40 (ddd, 1H), 8.08 (m, 1H); $^{13}$C NMR(90 MHz CDCl$_3$) d 27.03, 31.25, 41.98, 42.09, 106.56, 112.57, 137.27, 148.22, 159.00.

In a similar manner as described for the preparation of N-1-(5-bromopyrid-2-yl)-1-(3,4-dichlorobenzyl)ethane-1,2-diamine, a 60% dispersion of sodium hydride (1.27 g, 31.8 mmol), N-1-(pyrid-2-yl)butane-1,4-diamine (10.1 g, 30.3 mmol), and 4-bromobenzyl bromide (7.57 g, 30.3 mmol) in DMSO (60 mL) gave an oil. Flash chromatography on silica gel using CH$_2$Cl$_2$ 90: CH$_3$OH 5: Et$_3$N 5 yielded 4.29 g (57%) of N-1-(4-bromobenzyl)-1-(pyrid-2-yl)butane-1,4-diamine as a thick oil.

$^1$H NMR (90 MHz CDCl$_3$)d 1.45 (m, 4H, CH$_2$ and NH$_2$), 2.65 (t, 2H), 3.45 (t, 2H), 4.70 (s, 2H, ArCH$_2$), 6.95 (m, 2H), 7.25 (m, 5H), 8.15 (m, 1H); $^{13}$C NMR (90 MHz CDCl$_3$)d 24.66, 31.05, 41.94, 48.39, 50.99, 105.65, 111.88, 113.01, 120.49, 128.67, 130.24, 130.24, 130.73, 131.49, 137.23, 138.15, 148.07, 157.93.

A solution of N-1-(4-bromobenzyl)-1-(pyrid-2-yl)butane-1,4-diamine (1.11 g, 3.34 mmol) in THF (30 mL) was treated dropwise with a solution of 3-(imidazol-1-yl)propyl isothiocyanate (559 mg, 3.34 mmol) in THF (10 mL). After stirring overnight at room temperature under nitrogen, the solvent was removed under reduced pressure to afford an oil. The oil was dissolved in absolute ethanol and acidified with ethanolic hydrogen chloride. Addition of diethyl ether afforded a very hygroscopic solid. The solvents were removed under reduced pressure, and the residue was partitioned between 10% NaOH (100 mL) and methylene chloride (50 mL). The basic layer was extracted with methylene chloride (2×50 mL), and the combined organic extracts were washed with water (2×50 mL), dried (Na$_2$SO$_4$), filtered, and evaporated. The resulting oil was triturated with diethyl ether to yield 950 mg (57%) of a tan solid. Recrystallization from ethyl acetate-diethyl ether afforded 691 mg (41%) the title compound.

mp 122–124° C.; $^1$H NMR (90 MHz CDCl$_3$)d 1.63 (m, 4H), 2.07 (m, 2H), 3.55 (m, 6H), 4.01 (t, J=7.4 Hz, 2H, CH$_2$-imidazole), 4.66 (s, 2H, ArCH$_2$), 6.36–8.18 (m, 13H, ArH and NHC=SNH); $^{13}$C NMR (90 MHz CDCl$_3$)d 25.02, 26.16, 30.61, 41.28, 44.09, 44.16, 48.05, 51.19, 106.02, 112.14, 119.23, 120.64, 128.50, 129.09, 131.64, 136.95, 137.49, 147.84, 157.97, 182.89. Anal. Calcd for C$_{23}$H$_{29}$BrN$_6$S: C, 54.48; H, 5.84; N, 16.76. Found: C, 55.04; H, 5.90; N, 16.67.

Example 22

1-(4-(N-(3,4-Dichlorobenzyl)-N-(pyridin-2-yl)amino)butyl)-3-(3-(imidazol-1-yl)propyl)thiourea

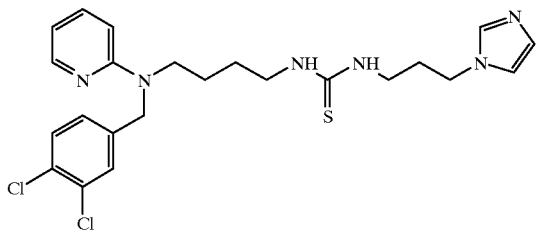

Following the general method, a 60% mineral oil dispersion of sodium hydride (613 mg, 15.3 mmol), N-1-(pyrid-2-yl) butane-1,4-diamine (2.41 g, 14.6 mmol), and 3,4-dichlorobenzyl bromide (3.50 g, 14.6 mmol) gave an oil. Purification by flash chromatography on silica gel using a solvent system of $CH_2Cl_2$ 50: $CH_3OH$ 50: concentrated $NH_4OH$ 1 afforded 0.950 g (20%) of a light green oil.

$^1$H NMR (90 MHz $CDCl_3$)d 1.52 (m, 4H), 2.02 (br s, 2H, $NH_2$), 2.70 (t, 2H), 3.43 (t, 2H), 4.71 (s, 2H, $ArCH_2$), 6.50 (m, 2H), 7.00–7.52 (m, 4H), 8.16 (m, 1H).

A solution of N-1-(3,4-dichlorobenzyl)-1-(pyrid-2yl) butane-1,4-diamine (900 mg, 2.79 mmol) in THF (20 mL) was treated dropwise with 3-(imidazol-1-yl)propyl isothiocyanate (470 mg, 2.79 mmol) in THF (15 mL). After stirring overnight under nitrogen, the solvent was removed under reduced pressure. The resulting residue was flash chromatographed on silica gel using a solvent system of $CH_2Cl_2$ 100: $CH_3OH$ 10: concentrated ammonium hydroxide 1 to yield a yellow foam. The foam was triturated with methanol-water to yield a white solid. Recrystallization from methylene chloride-diethyl ether afforded 659 mg (48%) of the title compound as a white, crystalline solid.

mp 112–113.5° C.; $^1$H NMR (90 MHz $CDCl_3$)d 1.60 (m, 4H), 2.08 (m, 2H), 3.50 (m, 6H), 4.00 (t, 2H), 4.63 (s, 2H, $ArCH_2$), 7.20 (ArH and NHC=SNH); $^{13}$C NMR (90 MHz $CDCl_3$)d 24.97, 26.17, 30.61, 41.39, 44.10, 44.69, 48.22, 50.87, 106.02, 112.47, 126.23, 128.66, 129.21, 130.61, 137.71, 139.23, 147.95, 182.95. Anal. Calcd for $C_{23}H_{28}Cl_2N_6S$: C, 56.20; H, 5.75; N, 17.10. Found: C, 56.03; H, 5.82; N, 16.99.

Example 23

1-(4-(N-(5-Bromopyridin-2-yl)-N-(3,4-dichlorobenzyl)amino)butyl)-3-(3-(imidazol-1-yl)propyl)thiourea

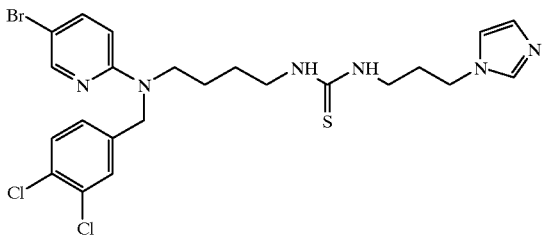

Using the method as described for the synthesis of N-1-(5-bromopyrid-2-yl)ethane-1,2-diamine, 2,5-dibromopyridine (10.0 g, 42.2 mmol), 1,4-diaminobutane (52.6 g, 597 mmol), and dry pyridine (4.20 g, 53.2 mmol) gave a brown oil. Vacuum distillation afforded 7.87 g (76%) of N-1-(5-bromopyrid-2-yl)butane-1,4-diamine as a colorless oil.

bp 165–170° C. (0.8 mm); $^1$H NMR (90 MHz $CDCl_3$)d 1.15–1.75 (m, 6H), 2.72 (t, 2H), 3.25 (br s, 2H, $NH_2$), 4.75 (br s, 1H, NH), 6.30 (d, J=9 Hz, pyridine H-3), 7.47 (dd, J=2.7 Hz, J=9 Hz, 1H, pyridine H-4), 8.10 (d, J=2.4 Hz, pyridine H-6); $^{13}$C NMR (90 MHz $CDCl_3$)d 26.87, 31.09, 41.87, 42.20, 108.07, 139.66, 148.71.

Using a similar method as described for N-1-(5-bromopyrid-2-yl)-1-(3,4-dichlorobenzyl)ethane-1,2-diamine, a 60% mineral oil dispersion of sodium hydride (1.20 g, 30.1 mmol), N-1-(5-bromopyrid-2-yl)butane-1,4-diamine (7.00 g, 28.7 mmol), and dichlorobenzyl chloride (5.62 g, 28.7 mmol) in DMSO (75 mL) gave an oil. Flash chromatography on silica gel using a solvent system of $CH_2Cl_2$ 50: $CH_3OH$ 50: concentrated $NH_4OH$ 1 yielded 2.32 g (20%) of N-1-(5-bromopyrid-2-yl)-1-(3,4-dichlorobenzyl)butane-1,4-diamine as an oil.

$^1$H NMR (90 MHz $CDCl_3$)d 1.50 (m, 4H, $CH_2$ and $NH_2$), 2.72 (t, 2H), 3.45 (t, 2H, $NCH_2$), 4.68 (s, 2H, $ArCH_2$), 6.35 (d, J=9 Hz, pyridine H-3), 7.00–7.55 (m, 4H, ArH), 8.15 (d, J=2.4 Hz, 1H, pyridine H-6); $^{13}$C NMR (90 MHz $CDCl_3$)d 24.48, 30.93, 41.87, 48.81, 59.76, 106.61, 107.10, 126.28, 128.77, 130.45, 139.12, 139.60, 148.60, 156.29.

A solution of N-1-(5-bromopyrid-2-yl)-1-(3,4-dichlorobenzyl)butane-1,4-diamine (1.01 g, 2.48 mmol) in THF (20 mL) was treated dropwise with 3-(imidazol-1-yl) propyl isothiocyanate (431 mg, 2.48 mmol) in THF (15 mL). After stirring overnight at room temperature under nitrogen, the solvent was removed under reduced pressure. The resulting residue was triturated with hexane-diethyl ether to afford a solid. Recrystallization from methylene chloride-diethyl ether gave 1.00 g (71%) the title compound as white crystals.

mp 139–141° C.; $^1$H NMR (90 MHz $CDCl_3$)d 1.61 (m, 4H), 2.07 (m, 2H), 3.50 (m, 6H), 4.00 (t, 2H), 4.62 (s, 2H, $ArCH_2$), 6.30 (d, J=9 Hz, 1H, pyridine H-3), 7.15 (m, 9H), 8.12 (d, 1H, pyridine H-6); $^{13}$C NMR (90 MHz $CDCl_3$)d 24.70, 26.33, 30.44, 41.28, 43.87, 44.64, 48.43, 50.97, 106.77, 107.32, 119.23, 126.17, 128.61, 130.62, 130.99, 136.89, 138.74, 139.77, 148.54, 182.94. Anal. Calcd for $C_{23}H_{27}BrCl_2N_6S$: C, 48.42; H, 4.78; N, 14.74. Found: C, 48.24; H, 4.89; N, 14.63.

Example 24

1-(4-(N-(5-Bromopyridin-2-yl)-N-(3,4-dichlorobenzyl)amino)butyl)-3-(3-(1H-imidazol-4-yl)propyl)thiourea

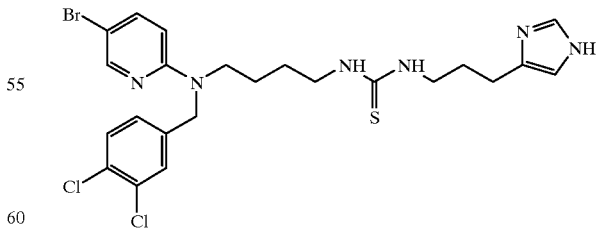

A mixture of DCC (858 mg, 4.16 mmol), carbon disulfide (1.85 g, 44.2 mmol), and N-1-(5-bromopyrid-2-yl)-1-(3,4-dichlorobenzyl)butane-1,4-diamine (1.68 g, 4.16 mmol) in THF (45 mL) afforded an oil. Purification by flash chromatography on silica gel using a solvent system of hexane 80:

EtOAc 20: Et$_3$N 1 gave 1.53 g (83%) of 4-[N-(5-bromopyrid-2-yl)-N-(3,4-dichlorobenzyl)]aminobutyl isothiocyanate as an oil.

$^1$H NMR (90 MHz CDCl$_3$)d 1.72 (m, 4H), 3.54 (m, 4H), 4.65 (s, 2H, ArCH$_2$), 6.32 (d, J=9 Hz, 1H, pyridine H-3), 6.97–7.50 (m, 4H), 8.16 (d, J=2.4 Hz, 1H, pyridin H-6); $^{13}$C NMR (90 MHz CDCl$_3$)d 24.32, 27.36, 44.80, 47.90, 51.62, 107.10, 126.18, 128.66, 130.56, 130.99, 132.67, 138.63, 139.71, 148.60, 156.18.

A suspension of 3-(1-triphenylmethyl-$^1$H-imidazol-4-yl) propylamine (0.50 g, 1.51 mmol) in THF (20 mL) was treated dropwise with a solution of 4-[N-(5-bromopyrid-2-yl)-N-(3,4-dichloroben-zyl)]aminobutyl isothiocyanate (0.67 g, 1.51 mmol) in THF (10 mL) under a nitrogen atmosphere. After stirring overnight at room temperature, the solvent was removed under reduced pressure to afford an oil. Flash chromatography on silica gel using CH$_2$Cl$_2$ 100: CH$_3$OH 2.5:Et$_3$N 2.5 afforded 0.62 g (71%) of a colorless oil. The oil was suspended in a mixture of 2 N HCl (50 mL) and ethanol (10 mL) and refluxed for 10 h. After cooling the precipitated triphenylmethanol was filtered, and the filtrate was evaporated. The residue was suspended in 2 N NaOH (40 mL), and the aqueous phase was extracted with methylene chloride (3×50 mL). The combined methylene chloride extracts were washed with water (3×50 mL), dried (Na$_2$SO$_4$), filtered, and evaporated to give 107 mg (18%) of the title compound as a hygroscopic solid:

mp 63–67° C.; $^1$H NMR (90 MHz CDCl$_3$)d 1.50–2.00 (m, 6H), 2.60 (m, 2H), 3.45 (br m, 6H), 4.63 (s, 2H, ArCH$_2$), 5.95–7.50 (m, 9H, ArH and NHC=SNH), 8.13 (d, J=2.4 Hz, 1H, pyridine H-6); $^{13}$C NMR (90 MHz CDCl$_3$)d 23.51, 24.65, 28.88, 43.39, 44.37, 48.59, 50.87, 106.72, 107.37, 115.12, 126.23, 128.66, 130.56, 130.89, 132.62, 134.14, 138.20, 148.49, 156.29, 181.65.

Example 25

1-(4-(N-(5-Bromopyridin-2-yl)-N-(3,4-dichlorobenzyl)amino)butyl)-3-(2-(1H-imidazol-4-yl)ethyl)thiourea

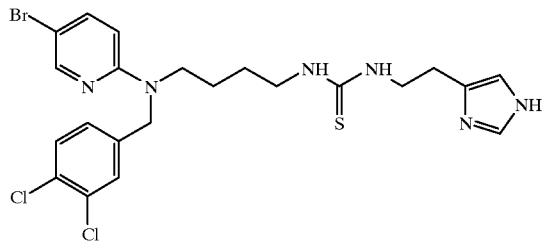

A suspension of histamine (352 mg, 3.17 mmol) in THF (10 mL) was cooled to 0–5° C. and treated dropwise with 4-[N-(5-bromopyrid-2-yl)-N-(3,4-dichlorobenzyl)] aminobutyl isothiocyanate (1.41 g, 3.17 mmol) in THF (20 mL). After stirring overnight, the solvent was removed under reduced pressure to yield an oil which was purified by flash chromatography using a solvent system of EtOAc 85:CH$_3$OH 15: concentrated NH$_4$OH 1. Fractions homogeneous by TLC were combined and evaporated under reduced pressure to afford 1.59 g (90%) of the title compound as a white foam.

$^1$H NMR (90 MHz CDCl$_3$)d 1.60 (m, 4H), 2.80 (m, 2H), 3.60 (m, 8H), 4.63 (s, 2H, ArCH$_2$), 6.37 (s, 1H), 6.79–7.55 (m, 7H, ArH and NHC=SNH), 8.16 (d, J=2.2 Hz, 1H); $^{13}$C NMR (90 MHz CDCl$_3$)d 24.65, 26.27, 26.65, 43.94, 44.21, 48.49, 50.87, 106.72, 107.37, 115.34, 126.17, 128.61, 130.56, 130.94, 132.62, 134.68, 139.82, 148.44, 156.29, 181.59.

Example 26

1-(5-(N-(5-Bromopyridin-2-yl)-N-(3,4-dichlorobenzyl)amino)pentyl)-3-(3-(1H-imidazol-4-yl)propyl)thiourea

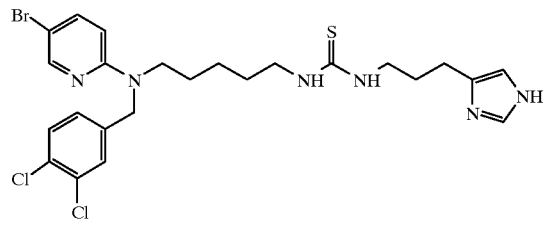

Following the general method as described for N-1-(5-bromopyrid-2-yl)ethane-1,2-diamine, 2,5-dibromopyridine (8.42 g, 35.5 mmol), pyridine (3.54 g, 44.8 mmol), and 1,5-diaminopentane (25.0 g, 244.7 mmol) gave an oil. Flash chromatography on silica gel using CH$_2$Cl$_2$ 50: CH$_3$OH 50:concentrated NH$_4$OH 1 as the solvent afforded 5.50 g (60%) of N-1-(5-bromopyrid-2-yl)pentane-1,5-diamine as an oil.

$^1$H NMR (90 MHz CDCl$_3$)d 1.50 (m, 6H), 1.85 (br s, 2H, NH$_2$), 2.72 (m, 2H), 3.25 (m, 2H), 4.70 (br s, 1H, NH), 6.30 (d, J=9 Hz, 1H, pyridine H-3), 7.47 (dd, 1H, pyridine H-4), 8.09 (d, 1H, pyridine H-6); $^{13}$C NMR (90 MHz CDCl$_3$)d 24.38, 29.40, 33.75, 41.88, 42.50, 106.88, 107.19, 140.00, 149.06, 157.50.

In a similar manner as described for the synthesis of N-1-(5-bromopyrid-2-yl)-1-(3,4-dichlorobenzyl)ethane-1,2-diamine, a 60% mineral oil dispersion of sodium hydride (940 mg, 23.4 mmol), N-1-(5-bromopyrid-2-yl)pentane-1, 5-diamine (5.50 g, 21.3 mmol), and 3,4-dichlorobenzyl chloride (4.60 g, 23.4 mmol) in DMSO (75 mL) afforded an oil. Purification by flash chromatography on silica gel using CH$_2$Cl$_2$ 50: CH$_3$OH 50: concentrated NH$_4$OH 1 as the solvent gave 1.46 g (16%) of N-1-(5-bromopyrid-2-yl)-1-(3,4-dichlorobenzyl)pentane-1,5-diamine as an oil.

$^1$H NMR (90 MHz CDCl$_3$)d 1.35 (m, 6H), 2.70 (m, 2H), 3.40 (t, 2H), 4.68 (s, 2H, ArCH$_2$), 6.35 (d, J=9 Hz, 1H, pyridine H-3), 7.35 (m, 4H, ArH), 8.15 (d, 1H, pyridine H-6); $^{13}$C NMR (90 MHz CDCl$_3$)d 24.38, 27.19, 33.75, 42.20, 49.06, 50.63, 106.25, 107.50, 126.25, 127.81, 130.94, 131.25, 131.90, 139.69, 140.00, 149.06, 156.56.

Following the general method, DCC (722 mg, 3.50 mmol), carbon disulfide (2.84 g, 37.3 mmol), and N-1-(5-bromopyrid-2-yl)-1-(3,4-dichlorobenzyl)pentane-1,5-diamine (1.46 g, 3.50 mmol) in THF (45 mL) gave an oil. Flash chromatography using hexane 80: EtOAc 20: Et$_3$N 1 afforded 1.38 g (86%) of 5-[N-(5-bromopyrid-2-yl)-N-(3,4-dichlorobenzyl)]aminopentyl isothiocyanate as an oil.

$^1$H NMR (90 MHz CDCl$_3$)d 1.60 (m, 6H), 3.47 (m, 4H), 4.69 (s, 2H, ArCH$_2$), 6.35 (d, J=9 Hz, 1H, pyridine H-3), 7.33 (m, 4H), 8.17 (d, 1H, pyridine H-6); $^{13}$C NMR (90 MHz CDCl$_3$)d 23.99, 26.44, 29.63, 44.86, 48.65, 50.92, 106.72, 107.05, 126.23, 128.72, 130.51, 132.62, 138.90, 139.66, 148.60, 156.24.

A solution of 3-[1-(triphenylmethyl)imidazol-4-yl] propylamine (1.02 g, 2.77 mmol) was dissolved in THF (20 mL) and treated dropwise with a solution of 5-[N-(5-bromopyrid-2-yl)-N-(3,4-dichlorobenzyl)]aminopentyl isothiocyanate (1.27 g, 2.77 mmol) in THF (40 mL) at 0–5° C. under a nitrogen atmosphere. The reaction was allowed to warm to room temperature and was stirred overnight. The reaction mixture was treated with additional 3-[1-(triphenylmethyl)imidazol-4-yl]propylamine (0.182 g, 0.495 mmol) and was refluxed for 24 h. Removal of the solvent afforded an oil which was purified by flash chromatography on silica gel using a solvent system of EtOAc 92: $CH_3OH$ 4: $Et_3N$ 4. Fractions homogeneous by TLC were combined and evaporated to yield 2.20 g of a foam. The trityl-protected thiourea was refluxed in 1 N HCl (50 mL) for 1.5 h, and the precipitated triphenylmethanol was removed by filtration. The filtrate was extracted with diethyl ether (2×100 mL), washed with water (100 mL), adjusted to pH 14 with 1 N NaOH, and extracted with with ethyl acetate (3×100 mL). The combined ethyl acetate extracts were washed with water (2×50 mL), dried ($Na_2SO_4$), filtered, and evaporated. The resulting residue was flash chromatographed on silica gel using EtOAc 85: $CH_3OH$ 15:concentrated $NH_4OH$ 1 as the eluent. Fractions homogeneous by TLC were combined and evaporated to yield 500 mg (31%) of the title compound as a foam.

$^1$H NMR (90 MHz $CDCl_3$)d 1.15–2.00 (m, 8H), 2.25 (m, 2H), 3.45 (m, 6H), 4.64 (s, 2H, $ArCH_2$), 6.25–8.13 (m, 10H, ArH and NHC=SNH); $^{13}$C NMR (90 MHz $CDCl_3$)d 23.86, 24.43, 26.98, 29.04, 43.61, 44.64, 48.97, 50.98, 106.78, 107.48, 126.44, 128.88, 130.67, 134.35, 139.17, 139.93, 148.65, 156.51, 181.70. Anal. Calcd. for $C_{24}H_{29}BrCl_2N_6S$: C, 49.32; H, 5.00; N, 14.38. Found: C, 49.12; H, 5.16; N, 14.15.

Example 27

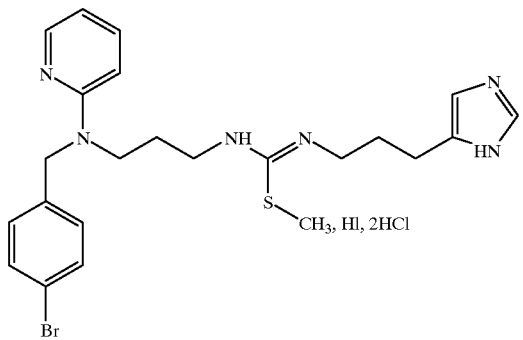

N1-[3-(Imidazol-4(5)-yl)propyl]-N2-[3-[(4-bromobenzyl)-N-(pyridin-2-yl)-amino]propyl]-S-methylisothiourea hydroiodide dihydrochloride To a solution of N1-[3-(imidazol-4(5)-yl)propyl]-N2-[3-[N-(4-bromobenzyl)-N-(pyridin-2-yl)-amino]propyl]-thiourea dihydrochloride (prepared as in example 1) (580 mg, 1.035 mmol) in absolute ethanol (50 ml) under an atmosphere of nitrogen was added iodomethane (0.10 ml, 1.279 mmol) and the reaction mixture was stirred for 60 h at room temperature. Iodomethane (0.025 ml, 0.32 mmol) was added and the reaction mixture stirred at room temperature for an additional 5 h. The volatiles were evaporated in vacuo affording 0.7 g (97%) of the title compound as an amorphous powder.

TLC: $R_f$=0.40 ($SiO_2$; Methanol/Triethylamine=75:25).

HPLC retention time=12.58 minutes (5 µM C18 4×250 mm column, eluting with a gradient of 15% acetonitrile/0.1 N aqueous ammonium sulphate to 25% acetonitrile/0.1 N aqueous ammonium sulphate, pH=2.5, over 10 minutes at room temperature)

$^1$H NMR (200 MHz, $D_3COD$) $\delta_H$ 2.12 (m, 4H), 2.71 (s, 3H, $SCH_3$), 2.85 (t, 2H) (m, 4H), 3.84 (m, 2H), 4.95 (s, 2H, $CH_2$—Ph), 7.02 (t, 1H), 7.22 (d, 2H), 7.30 (d, 1H), 7.42 (bs, 1H), 7.52 (d, 2H), 7.98 (d, 1H), 8.05 (bs, 1H), 8.80 (d, 1H).

What is claimed is:

1. A compound of general formula Ia or Ib

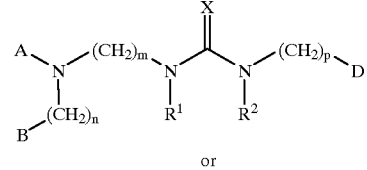

Ia or

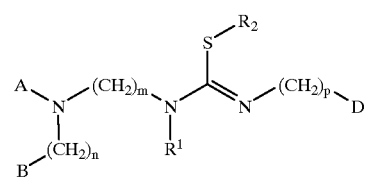

Ib wherein m is 2, 3, 4, 5 or 6, n is 1, 2 or 3, p is 1, 2, 3, 4, 5 or 6, $R^1$ and $R^2$ are independently hydrogen or $C_{1-6}$-alkyl optionally substituted with halogen, amino, hydroxy, alkoxy or aryl, X is =S, =O, =NH, =NCOPh or =N(CN), A is aryl optionally substituted with halogen, amino, hydroxy, nitro, $C_{1-6}$-alkyl, $C_{1-6}$-alkoxy or aryl, B is aryl optionally substituted with halogen, amino, hydroxy, $C_{1-6}$-alkyl, $C_{1-6}$-alkoxy or aryl, D is aryl, amino, optionally substituted with halogen, amino, hydroxy, $C_{1-6}$-alkyl, $C_{1-6}$-alkoxy or aryl, or a pharmaceutically acceptable salt thereof.

2. A compound of general formula Ia

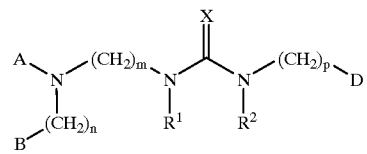

Ia wherein m is 2, 3, 4, 5 or 6, n is 1, 2 or 3, p is 1, 2, 3, 4, 5 or 6, $R^1$ and $R^2$ are independently hydrogen or $C_{1-6}$-alkyl optionally substituted with halogen, amino, hydroxy, alkoxy or aryl, X is =S, =O, =NH, =NCOPh or =N(CN), A is aryl optionally substituted with halogen, amino, hydroxy, nitro, $C_{1-6}$-alkyl , $C_{1-6}$-alkoxy or aryl, B is aryl optionally substituted with halogen, amino, hydroxy, $C_{1-6}$-alkyl, $C_{1-6}$-alkoxy or aryl, D is aryl, amino, optionally substituted with halogen, amino, hydroxy, $C_{1-6}$-alkyl, $C_{1-6}$-alkoxy or aryl, or a pharmaceutically acceptable salt thereof.

3. The compound according to claim 1, wherein X is =S, =NH, =NCOPh, or =N—CN, preferably =S, =NH or =NCOPh.

4. The compound according to claim 1, wherein A is pyridinyl, quinolinyl, isoquinolinyl, pyrimidinyl, pyrazinyl, pyridazinyl or triazinyl optionally substituted with halogen, amino, hydroxy, nitro, $C_{1-6}$-alkyl, $C_{1-6}$-alkoxy or aryl.

5. The compound according to claim 4, wherein A is pyridine or quinoline optionally substituted with halogen, amino, hydroxy, nitro, $C_{1-6}$-alkyl, $C_{1-6}$-alkoxy or aryl, preferably pyridine, pyridine substituted with bromo or nitro, or quinoline.

6. The compound according to claim 1, wherein B is phenyl, naphthyl, quinolinyl, isoquinolinyl, indolyl, thienyl, furanyl or pyridinyl optionally substituted with halogen, amino, hydroxy, $C_{1-6}$-alkyl, $C_{1-6}$-alkoxy or aryl.

7. The compound according to claim 6, wherein B is phenyl or naphthyl optionally substituted with halogen, amino, hydroxy, nitro, $C_{1-6}$-alkyl, $C_{1-6}$-alkoxy or aryl, preferably phenyl substituted with bromo or two chloro, or naphthyl.

8. The compound according to claim 1, wherein D is amino, imidazolyl, pyridinyl, pyrimidinyl, piperidinyl, pyrrolidinyl, piperazinyl, pyridinylamino, pyrimidinylamino, piperidinylamino, pyrrolidinylamino, piperazinylamino, morpholinyl, triazolyl, tetrazolyl, thiadiazolyl, isoxazolyl or oxadiazolyl optionally substituted with halogen, amino, hydroxy, $C_{1-6}$-alkyl, $C_{1-6}$-alkoxy or aryl.

9. The compound according to claim 8, wherein D is imidazole, morpholinyl, pyrrolidinyl, amino or pyridinylamino optionally substituted with halogen, amino, hydroxy, $C_{1-6}$-alkyl, $C_{1-6}$-alkoxy or aryl, preferably imidazole, morpholinyl, dimethylamino, pyrrolidinyl, pyridinylamino, amino or pyridinyl.

10. The compound according to claim 1, wherein $R_1$ and $R_2$ independently are hydrogen or $C_{1-6}$-alkyl, preferably hydrogen or methyl.

11. The compound according to claim 1 selected from the group consisting of

N1-[3-(Imidazol-4(5)-yl)propyl]-N2-[3-[N-(4-bromobenzyl)-N-(pyridin-2-yl)-amino]propyl]-S-methylisothiourea, or the hydroiodide, dihydrochloride salt thereof;

1-(3-(N-(5-Bromopyridin-2-yl)-N-(3,4-dichlorobenzyl)amino)propyl)-3-(3-(1H-imidazol-4-yl)propyl)thiourea;

1-(3-(N-(4-Bromobenzyl)-N-(pyridin-2-yl)amino)propyl)-3-(3-(1H-imidazol-4-yl)propyl)thiourea, or the dihydrochloride salt thereof;

1-(4-Aminobutyl)-3-(3-(N-(5-bromopyridin-2-yl)-N-(3,4-dichlorobenzyl)amino)propyl)thiourea;

1-(3-(N-(5-Bromopyridin-2-yl)-N-(3,4-dichlorobenzyl)amino)propyl)-3-(3-(N-(pyridin-2-yl)amino)propyl)thiourea;

1-(3-(N-(4-Bromobenzyl)-N-(pyridin-2-yl)amino)propyl)-3-(3-N,N-dimethylaminopropyl)thiourea;

1-(3-(N-(4-Bromobenzyl)-N-(pyridin-2-yl)amino)propyl)-3-(3-(morpholin-4-yl)propyl)thiourea;

1-(3-(N-(4-Bromobenzyl)-N-(pyridin-2-yl)amino)propyl)-3-(3-(imidazol-1-yl)propyl)thiourea, or the dihydrobromide salt thereof;

1-(4-(N-(4-Bromobenzyl)-N-(pyridin-2-yl)amino)butyl)-3-(3-(imidazol-1-yl)propyl)thiourea;

1-(4-(N-(3,4-Dichlorobenzyl)-N-(pyridin-2-yl)amino)butyl)-3-(3-(imidazol-1-yl)propyl)thiourea;

1-(3-(N-(5-Bromopyridin-2-yl)-N-(3,4-dichlorobenzyl)amino)propyl)-3-(3-(imidazol-1-yl)propyl)thiourea;

1-(4-(N-(5-Bromopyridin-2-yl)-N-(3,4-dichlorobenzyl)amino)butyl)-3-(3-(imidazo-1-yl)propyl)thiourea;

1-(3-(N-(4-Bromobenzyl)-N-(pyridin-2-yl)amino)propyl)-3-(4-(N-(pyridin-2-yl)amino)propyl)thiourea;

1-(4-(N-(5-Bromopyridin-2-yl)-N-(3,4-dichlorobenzyl)amino)butyl)-3-(3-(1H-imidazol-4-yl)propyl)thiourea;

1-(5-(N-(5-Bromopyridin-2-yl)-N-(3,4-dichlorobenzyl)amino)pentyl)-3-(3-(1H-imidazol-4-yl)propyl)thiourea;

1-(4-(N-(5-Bromopyridin-2-yl)-N-(3,4-dichlorobenzyl)amino)butyl)-3-(2-(1H-imidazol-4-yl)ethyl)thiourea;

1-(2-(N-(5-Bromopyridin-2-yl)-N-(3,4-dichlorobenzyl)amino)ethyl)-3-(2-(1H-imidazol-4-yl)ethyl)thiourea;

1-(2-(N-(5-Bromopyridin-2-yl)-N-(3,4-dichlorobenzyl)amino)ethyl)-3-(3-(1H-imidazol-4-yl)propyl)thiourea;

1-(3-(N-(5-Bromopyridin-2-yl)-N-((naphth-1-yl)methyl)amino)propyl)-3-(3-(1H-imidazol-4-yl)propyl)thiourea;

1-(4-Aminobutyl)-3-(3-(N-(5-bromopyridin-2-yl)-N-((naphth-1-yl)methyl)amino)propyl)thiourea;

1-(3-(N-(5-Bromopyridin-2-yl)-N-(3,4-dichlorobenzyl)amino)propyl)-3-(2-(pyrid-2-yl)ethyl)thiourea;

1-(3-(N-(5-Bromopyridin-2-yl)-N-(3,4-dichlorobenzyl)amino)propyl)-3-(3-(pyrrolidin-1-yl)propyl)thiourea;

1-(4-Aminobutyl)-3-[3-[N-(5-bromopyrid-2-yl)]-[N-(3,4-dichlorobenzyl)]aminopropyl]thiourea;

1-(3-(N-(5-Bromopyridin-2-yl)-N-(3,4-dichlorobenzyl)amino)propyl)-3-(4-(N-(pyridin-2-yl)amino)propyl)thiourea;

1-(2-(N-(5-Bromopyridin-2-yl)-N-(3,4-dichlorobenzyl)amino)ethyl)-3-(3-dimethylaminopropyl)thiourea;

1-(2-(N-(5-Bromopyridin-2-yl)-N-(3,4-dichlorobenzyl)amino)ethyl)-3-(3-(pyrrolidin-1-yl)propyl)thiourea;

1-(2-(N-(5-Nitropyridin-2-yl)-N-(3,4-dichlorobenzyl)amino)ethyl)-3-(3-(1H-imidazol-4-yl)propyl)thiourea;

1-[3-[((4-Bromobenzyl)pyridin-2-yl)amino]propyl]-3-[2-(1H-imidazol-4-yl)propyl]guanidine;

1-[3-[((4-Bromobenzyl)pyridin-2-yl)amino]propyl]-3-[2-(1H-imidazol-4-yl)ethyl]guanidine;

1-[3-[((4-Bromobenzyl)pyridin-2-yl)amino]propyl]-3-[3-(1H-imidazol-4-yl)propyl]guanidine;

1-[3-[((4-Bromobenzyl)pyridin-3-yl)amino]propyl]-3-[3-(1H-imidazol-4-yl)ethyl]guanidine;

1-[3-[N-(4-Bromobenzyl)-N-(pyrimidin-2-yl)amino]propyl]-3-[3-(1H-imidazol-4-yl)propyl]guanidine;

1-[3-[N-(4-Bromobenzyl)-N-(pyridin-2-yl)amino]propyl]-3-[3-(imidazol-1-yl)propyl]guanidine;

1-[3-[N-(4-Bromobenzyl)-N-(pyridin-2-yl)amino]propyl]-3-[3-[N-(pyridin-2-yl)amino]propyl]guanidine;

1-[3-[N-(4-Bromobenzyl)-N-(pyridin-2-yl)amino]propyl]-3-[2-(pyridin-2-yl)ethyl]guanidine;

1-[3-[N-(4-Bromobenzyl)-N-(pyridin-2-yl)amino]propyl]-3-[3-(morpholin-4-yl)propyl]guanidine;

1-Methyl-1-[3-(N,N-dimethylamino)propyl]-3-[3-[N-(4-bromobenzyl)-N-(pyridin-2-yl)amino]propyl]guanidine;

1-Benzoyl-2-[3-[((4-bromobenzyl)quinol-2-yl)amino]propyl]-3-[3-(1H-imidazol-4-yl)propyl]guanidine;

1-[3-[N-(4-Bromo-benzyl)-N-(quinolin-2-yl)amino]-propyl]-3-[3-(1H-imidazol-4-yl)propyl]guanidine, or the trihydrochloride salt thereof; or 1-[3-[N-(4-bromobenzyl)-N-(quinolin-2-yl)amino]propyl]-2-Benzoyl-3-[3-(1H-imidazol-4-yl)propyl]guanidine.

12. A pharmaceutical composition comprising, a compound according to claim 1 together with a pharmaceutically acceptable carrier or diluent.

13. The composition according to claim 12 in unit dosage form, comprising from about 10 to about 200 mg of the compound of the general formula I or a pharmaceutically acceptable salt thereof.

14. A method of mediating the biological effect of somatostatin agonists or antagonist, the method comprising administering to a subject in need thereof an effective amount of a compound according to claim 1.

15. A method according to claim 14, wherein the effective amount of the compound according to any one of the preceeding compound claims or pharmaceutically acceptable salt or ester thereof is in the range of from about 0.0001 to about 100 mg/kg body weight per day, preferably from about 0.001 to about 50 mg/kg body weight per day.

16. Use of a compound according to any one of the preceeding compound claims for the development of pharmaceutical, therapeutic, and diagnostic techniques.

17. A method for producing a prophylactic or therapeutic response in a mammal, comprising administering to the mammal a pharmaceutically effective amount of one or more compounds according to claim 1.

* * * * *